(12) United States Patent
Shi

(10) Patent No.: US 8,895,531 B2
(45) Date of Patent: Nov. 25, 2014

(54) 2'-FLUORONUCLEOSIDE PHOSPHONATES AS ANTIVIRAL AGENTS

(75) Inventor: Junxing Shi, Duluth, GA (US)

(73) Assignee: RFS Pharma LLC, Tucker, GA (US)

( * ) Notice: Subject to any disclaimer, the term of this patent is extended or adjusted under 35 U.S.C. 154(b) by 1044 days.

(21) Appl. No.: 11/726,686

(22) Filed: Mar. 22, 2007

(65) Prior Publication Data
US 2007/0225249 A1 Sep. 27, 2007

Related U.S. Application Data

(60) Provisional application No. 60/785,356, filed on Mar. 23, 2006.

(51) Int. Cl.
| | | |
|---|---|---|
| A61K 31/70 | (2006.01) |
| C07H 17/04 | (2006.01) |
| C07H 19/10 | (2006.01) |
| C07H 19/06 | (2006.01) |
| C07H 19/04 | (2006.01) |
| C07H 19/20 | (2006.01) |
| C07H 19/16 | (2006.01) |
| C07F 9/6561 | (2006.01) |
| C07F 9/6558 | (2006.01) |

(52) U.S. Cl.
CPC ............ *C07H 19/04* (2013.01); *C07H 19/10* (2013.01); *C07H 19/06* (2013.01); *C07H 19/20* (2013.01); *C07H 19/16* (2013.01); *C07F 9/65616* (2013.01); *C07F 9/65586* (2013.01)
USPC ................. 514/47; 514/48; 514/51; 536/26.1

(58) Field of Classification Search
None
See application file for complete search history.

(56) References Cited

U.S. PATENT DOCUMENTS

| | | | |
|---|---|---|---|
| 4,000,137 A | 12/1976 | Dvonch et al. |
| 4,211,773 A | 7/1980 | Lopez et al. |
| 4,336,381 A | 6/1982 | Nagata et al. |
| 4,625,020 A | 11/1986 | Brundidge et al. |
| 4,666,892 A | 5/1987 | Fox et al. |
| 5,034,518 A | 7/1991 | Montgomery et al. |
| 5,041,449 A | 8/1991 | Belleau et al. |
| 5,047,407 A | 9/1991 | Belleau et al. |
| 5,128,458 A | 7/1992 | Montgomery et al. |
| 5,149,794 A | 9/1992 | Yatvin et al. |
| 5,194,654 A | 3/1993 | Hostetler et al. |
| 5,210,085 A | 5/1993 | Liotta et al. |
| 5,223,263 A | 6/1993 | Hostetler et al. |
| 5,246,924 A | 9/1993 | Fox et al. |
| 5,256,641 A | 10/1993 | Yatvin et al. |
| 5,336,764 A | 8/1994 | Marquez et al. |
| 5,411,947 A | 5/1995 | Hostetler et al. |
| 5,424,416 A | 6/1995 | Jones |
| 5,426,183 A | 6/1995 | Kjell |
| 5,446,029 A | 8/1995 | Eriksson et al. |
| 5,463,092 A | 10/1995 | Hostetler et al. |
| 5,543,389 A | 8/1996 | Yatvin et al. |
| 5,543,390 A | 8/1996 | Yatvin et al. |
| 5,543,391 A | 8/1996 | Yatvin et al. |
| 5,554,728 A | 9/1996 | Basava et al. |
| 5,565,438 A | 10/1996 | Chu et al. |
| 5,567,688 A | 10/1996 | Chu et al. |
| 5,587,362 A | 12/1996 | Chu et al. |
| 5,672,697 A * | 9/1997 | Buhr et al. ................. 536/26.7 |
| 5,814,639 A | 9/1998 | Liotta et al. |
| 5,817,799 A | 10/1998 | Marquez et al. |
| 5,886,179 A | 3/1999 | Arimilli et al. |
| 5,914,331 A | 6/1999 | Liotta et al. |
| 5,919,816 A * | 7/1999 | Hausheer et al. ............ 514/449 |
| 6,348,587 B1 | 2/2002 | Schinazi et al. |
| 2004/0023921 A1 | 2/2004 | Hong |
| 2005/0215513 A1 | 9/2005 | Boojamra |
| 2007/0087960 A1* | 4/2007 | Storer et al. .................... 514/8 |

FOREIGN PATENT DOCUMENTS

| | | |
|---|---|---|
| EP | 0 463 470 | 10/1982 |
| EP | 0 292 023 | 11/1988 |
| EP | 0 316 017 | 5/1989 |
| EP | 0337 713 | 10/1989 |
| EP | 0 350 287 | 1/1990 |
| EP | 0 352 248 | 1/1990 |
| EP | 0 357 571 | 3/1990 |
| EP | 0 369 409 | 5/1990 |
| EP | 0 382 526 | 8/1990 |
| EP | 0 398 231 | 11/1990 |
| EP | 0 409 227 A2 | 1/1991 |
| JP | 51-146482 | 12/1976 |
| JP | 53-084981 A | 7/1978 |
| JP | 50-50383 | 3/1993 |
| JP | 50-50384 | 3/1993 |
| JP | 50-64281 | 3/1993 |
| WO | WO-88/09001 | 11/1988 |
| WO | WO-89/02733 | 4/1989 |
| WO | WO-90/00555 | 1/1990 |
| WO | WO-2004/002999 | 12/1990 |
| WO | WO-2004/003000 | 12/1990 |

(Continued)

OTHER PUBLICATIONS

Vippagunta et al., Adv Drug Deliv. rev. (48) pp. 3-26 , 2001.*
Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Cihlar, T., "GS9148: A Novel Nucleotide Against HIV-1 Variants with Drug-Resistance Mutations in Reverse Transcriptase," CROI 2006 Abstract #45.
International Search Report , from PCT/US07/007304, mailed Jan. 18, 2008.
Alter, H.J., J. Gastro. Hepatol. 1:78-94 (1990).
Alter, H.J. et al., N. Eng. J. Med. 321:1494-1500 (1990).
Balakrishna et al., Inhibition of Hep B Virus by a Novel L-Nucleotide, 2'-Fluoro-5-Methyl-B-L-arabinofuranosyl Uracil, Antimicrobial Agents and Chemotherapy 380-356 (Feb. 1996).
Belen'kii, M.S. et al., Antiviral Res. 25:1-11 (1994).

(Continued)

*Primary Examiner* — Traviss C McIntosh, III
(74) *Attorney, Agent, or Firm* — David Bradin

(57) ABSTRACT

The present invention includes compounds and compositions of ®-2'-fluoronucleoside phosphonates, as well as methods to treat HIV, HBV, HCV or abnormal cellular proliferation comprising administering said compounds or compositions.

20 Claims, No Drawings

(56) References Cited

FOREIGN PATENT DOCUMENTS

| WO | WO 91/16920 | 11/1991 |
|----|----|----|
| WO | WO-91/18914 | 12/1991 |
| WO | WO-91/19721 | 12/1991 |
| WO | WO-92/08727 | 5/1992 |
| WO | WO 92/13869 | 8/1992 |
| WO | WO-93/00910 | 1/1993 |
| WO | WO 94/01138 | 1/1994 |
| WO | WO-94/14831 | 7/1994 |
| WO | WO-94/26273 | 11/1994 |
| WO | WO-96/15132 | 5/1996 |
| WO | WO 98/42351 | 10/1998 |
| WO | WO-99/43691 | 9/1999 |
| WO | WO-01/90121 | 11/2001 |
| WO | WO-01/92282 | 12/2001 |
| WO | WO-2004/002422 | 1/2004 |
| WO | WO 2004/096233 | 11/2004 |
| WO | WO 2004/096235 | 11/2004 |
| WO | WO2004/096286 | * 11/2004 |
| WO | WO 2004/096286 | 11/2004 |
| WO | WO-2005/003147 | 1/2005 |
| WO | WO2006/015261 | * 2/2006 |
| WO | WO 2006/015261 | 2/2006 |

OTHER PUBLICATIONS

Chu, et al., "Use of 2'-Fluoro-5-methyl-B-L-arabinofuranosyluracil as a Novel Antiviral Agent for Hepatitis B Virus and Epstein-Barr Virus," Antimicrobial Agents and Chemotherapy 979-81 (Apr. 1995).

Hong, C.I. et al., "Nucleoside Conjugates as Potential Antitumor Agents 3 Synthesis and Antitumor Activity of 1-(B-D-arbinofuranosyl) Cytosine Conjugates of Corticosteroids and Selected Lipophilic Alcohols," J. Med. Chem. 28:171-77 (1980).

Montgomery, et al., 9-(2-Deoxy-2-fluoro-B-D-arabinofuranasyl)-guanine: A Metabolically Stable Cytotoxic Analogue of 2'-Deoxyguanosine.

Perkins, R.M., "Activity of BRL47923 and its Oral Prodrug, SB203657A Against a Rauscher Murine Leukaemia Virus Infection in Mice," Antiviral Res. 20;84 (Supp I).

Saneyoshi, M. et al. "Synthetic Nucleosides and Nucleotides. XVI. Synthesis and Biological Evaluations of a Series of 1-B-D-arabinofuranosylcytosine 5'-alky or Arylphosphates," Chem. Pharm. Bull 28:2915-23 (1980).

Shuto, S. et al., "A Facile One-Step Synthesis of 5' Phosphatidylnucleosides by an Enzymatic Two-Phase Reaction," Tetrahedron Lett. 28:199-202 (1987).

Shuto, S. et al., Pharm. Bull. 36:209-17 (1988).

Wang, S. et al., "Activity of Nucleoside and Non-Nucleoside Reverse Transcriptase Inhibitors (NNRTI) Against Equine Infectious Anemia Virus (EIAV)," First Natl Conf. on Human Retro Viruses and Related Infections, Washington D.C. (Dec. 12-16, 1993).

Zemlicka et al., J. Am. Chem. Soc. 94:3212 (1972).

Cosyn, L. et al., "Synthesis and P2Y receptor activity of nucleoside 5'-phosponate derivatives," Bioorg. Med. Chem. Lett., author manuscript, available in PMC Jun. 1, 2010 (1-11).

Shaw, et al., "Oral bioavailability of PMEA from PMEA prodrugs in male Sprague-Dawley rats." 9th Annual AAPS Meeting., 1994, San Diego, CA (Abstract).

Schinazi, et al., "Selective Inhibition of Human Immunodeficiency viruses by Racemates and Enantiomers of cis-5-Fluoro-l-[2-(Hydroxymethyl)-1,3-Oxathiolane-5-yl]-Cytosine" Antimicrobial Agents and Chemotherapy, 1992, pp. 2423-2431.

Furman, et al., "The Anti-Hepatitis B Virus Activities, Cytotoxicities, and Anabolic Profiles of the (−) and (+) Enantiomers of cis-5-Fluoro-1-[2-(Hydroxymethyl)-1,3-oxathiolane-5-yl]-Cytosine" Antimicrobial Agents and Chemotherapy, 1992, pp. 2686-2692.

Cheng, et al., Journal of Biological Chemistry, 267(20), 1992, pp. 13938-13942.

Alter M. J. et al., J.A.M.A., 1990, 264:2231-2235.

Alter M.J. et al., N. Engl. J. Med., 1992, 327:1899-1905.

Su, et al., Nucleosides. 136. Synthesis and Antiviral Effects of Several 1-(2-Deoxy-2-fluoro-®-D-arabinofuranosyl)-5-alkyluracils. Some Structure-Activity Relationships, J. Med. Chem., 1986, 29:151-154.

Borthwick, et al., "Synthesis and Enzymatic Resolution of Carbocyclic 2'-Ara-fluoro-Guanosine: A Potent New Anti-Herpetic Agent", J. Chem. Soc., Chem. Commun, 1988: 656-658.

Wantanabe, et al., "Synthesis and Anti-HIV Activity of 2'-"Up"-Fluoro Analogues of Active Anti-Aids Nucleosides 3'-Azido-3'-deoxythymidine (AZT) and 2',3'-deoxythymidine (AZT) and 2',3'-dideoxycytidine (DDC)", J. Med. Chem. 1990, 33:2145-2150.

Martin, et al., "Synthesis and Antiviral Activity of Monofluoro and Difluoro Analogues of Pyrimidine Deoxyribonucleosides against Human Immunodeficiency Virus (HIV-1)", J. Med. Chem. 1990, 33:2137-2145.

Sterzycki, et al., "Synthesis and Anti-HIV Activity of Several 2'-Fluoro-Containing Pyrimidine Nucleosides", J. Med. Chem., 1990, 33(8): 2150-2157.

Kinetic Studies of 2',2'-difluorodeoxycytidine (Gemcitabine) with Purified Human Deoxycytidine Kinase and Cytidine Deaminase, BioChemical Pharmacology, 1993, 45(9): 1857-1861.

De Clercq, et al., "A novel selective broad-spectrum anti-DNA virus agent", Nature, 1986, 323: 464-467.

Balzarini, et al., "Marked in vivo antiretrovirus activity of 9-(2-phosphonylmethoxyethyl)-adenine, a selective anti-human immunodeficiency virus agent", Proc. Natl. Acad. Sci. U.S.A. 1989, 86:332-336.

Balzarini, et al., "Differential antiherpesvirus and antiretrovirus effects of the (S) and (R) enantiomers of acyclic nucleoside phosphonates: Potent and selective in vitro and in vivo antiretrovirus activities of (R)-9-(2-phosphonomethoxypropyl)-2,6-diaminopurine", Antimicrob. Agents Chemother. 1993, 37:332-338.

Sellon D.C., "Equine Infectious Anemia," Vet. Clin. North Am. Equine Pract. United States, 1993, 9:321-336.

Philpott, et al., "Evaluation of 9-(2-phosphonylmethoxyethyl) adenine therapy for feline immunodeficiency virus using a quantitative polymerase chain reaction," Vet. Immunol. Immunopathol. 1992, 35:155-166.

R. Jones, et al., Antiviral Research, 1995, 27:1-17.

Kucera, L.S., et al., "Novel membrane-interactive ether lipid analogs that inhibit infectious HIV-1 production and induce defective virus formation.", AIDS Res. Hum. Retro Viruses., 1990, 6:491-501.

Piantadosi, C., et al., "Synthesis and evaluation of novel ether lipid nucleoside conjugates for anti-HIV activity.", J. Med. Chem., 1991, 34:1408-1414.

Hosteller, et al., "Greatly enhanced inhibition of human immunodeficiency virus type 1 replication in CEM and HT4-6C cells by 3'-deoxythymidine diphosphate dimyristoylglycerol, a lipid prodrug of 3,-deoxythymidine", Antimicrob. Agents Chemother., 1992, 36:2025-2029.

Hosetler, et al., "Synthesis and antiretroviral activity of phospholipid analogs of azidothymidine and other antiviral nucleosides", J. Biol. Chem., 1990, 265:6112-6117.

Ho, D.H.W., "Distribution of Kinase and deaminase of 1®-D-arabinofuranosylcytosine in tissues of man and muse", Cancer Res., 1973, 33:2816-2820.

Holy, A., "Isopolar phosphorous-modified nucleotide analogues," In: De Clercq (Ed.), Advances in Antiviral Drug Design, vol. I, JAI Press, 1993, 179-231.

Hong, C.I., et al., "Synthesis and antitumor activity of 1-®-D-arabino-furanosylcytosine conjugates of cortisol and cortisone", Bicohem. Biophys. Rs. Commun., 1979, 88:1223-1229.

Hosteller, K.Y. et al., J. Biol. Chem. , 265:6112-6117.

Hosteller, K.Y., et al., "Phosphatidylazidothymidine: mechanism of antiretroviral action in CEM cells", J. Biol Chem., 1991, 11714-11717.

Hosteller, et al., "Antiviral activity of phosphatidyl-dideoxycytidine in hepatitis B-infected cells and enhanced hepatic uptake in mice", Antiviral Res., 1994, 24:59-67.

Hosteller, et al., "Phosphatidylazidothymidine and phosphatidyl-ddC: Assessment of uptake in mouse lymphoid tissues and antiviral activities in human immunodeficiency virus-infected cells and in rauscher leukemia virus-infected mice", Antimicrobial Agents Chemother., 1994, 38:2792-2797.

Hunston, et al., "Synthesis and biological properties of some cyclic phosphotriesters derived from 2'-deoxy-5-flourouridine", J. Med. Chem., 1984, 27:440-444.

(56) References Cited

OTHER PUBLICATIONS

Ji, et al., "Monophosphoric acid esters of 7-®-hydroxycholesterol and of pyrimidine nucleoside as potential antitumor agents: synthesis and preliminary evaluation of antitumor activity", *J. Med. Chem.*,1990, 33:2264-2270.
Jones, et al., "Synthesis, properties, and biological activity of some nucleoside cyclic phosphoramidates", *J. Chem. Soc. Perkin Trans. I*, 1984, 1471-1474.
Kataoka, et al., "Alkylated cAMP derivatives; selective synthesis and biological activities", *Nucleic Acids Res. Sym. Ser.*, 1989, 21:1-3.
Kataoka, et al., "(cAMP) benzyl and methyl triesters", *Heterocycles*, 32:1351-1356.
Kinchington, et al., "Comparison of antiviral effects of zidovudine phosphoramidate and phosphorodiamidate derivates against HIV and ULV in vitro", *Antiviral Chem. Chemother.*, 1992,3:107-112.
Kodama, et al., "Antitumor activity and pharmacology of 1-®-D-arabinofuranosylcytosine-5'-stearylphosphate; an orally active derivative of 1-®-D-arabinofuranosylcytosine", *Jpn. J. Cancer Res.*, 1989, 80:679-685.
Korty, et al., "The effects of adenosine- and guanosine 3',5' phosphoric and acid benzyl esters on guinea-pig ventricular myocardium", *Naunyn-Schmiedeberg's Arch. Pharmacol.*, 1979, 310:103-111.
Kumar, et al., "Synthesis and biological evaluation of some cyclic phosphoramidate nucleoside derivatives", *J. Med. Chem*,1990, 33:2368-2375.
LeBec, et al., "Synthesis of lipophilic phosphate triester derivatives of 5-fluorouridine an arabinocytidine as anticancer prodrugs", *Tetrahedron Lett.*, 1991, 32:6553-6556.
Lichtenstein, J., et al., "The metabolism of exogenously supplied nucleotides by *Escherichia coli.*", *J. Biol. Chem.*, 1960, 235:457-465.
McGigan, et al., "Synthesis and biological evaluation of some phosphate triester derivatives of the anti-viral drug Ara", *Nucleic Acids Res.* , 1989, 17:6065-6075.
McGuigan, C., "Synthesis and evaluation of some novel phosphoramidate derivatives of 3'-azido-3'-deoxythymidine (AZT) as anti-HIV compounds", *Antiviral Chem. Chemother.*, 1990, 1:107-113.
McGuigan, et al., "Synthesis and anti-HIV activity of some novel substituted dialkyl phosphate derivatives of AZT and ddCyd." *Antiviral Chem. Chemother.*, 1990, 1:355-360.
McGuigan, et al., "Synthesis of some novel dialkyl phosphate derivative of 3'-modified nucleosides as potential anti-AIDS drugs", *Antiviral Chem. Chemother.* 1990, 1: 25-33.
McGuigan, et al., "Synthesis and anti-HIV activity of some haloalkyl phosphoramidate derivatives of 3'-azido-3'-deoxythylmidine (AZT); potent activity of the trichloroethyl methoxyalaninyl compound", *Antiviral Res.* 1991, 15: 255-263.
McGuigan, et al., "Intracellular delivery of bioactive AZT nucleotides by aryl phosphate derivatives of AZT." *J. Med. Chem.*, 1993, 36:1048-1052.
Wagner, et al., "Pronucleotides: towards the in vivo delivery of antiviral and anticancer nucleotides", *Med. Res. Rev.* 2000, 20:417-451.
Meier, C., "CycloSal-pronucleotides-design of chemical Trojan horses", *Mini Rev. Med. Chem.*, 2002, 2:219-234.
Cahard, et al., "Aryloxy phosphoramidate trimesters as pro-tides", *Mini Rev. Med. Chem.*, 2004, 4:371-381.
Peyrottes, et al., "SATE pronucleotide approaches: an overview", *Mini Rev. Med. Chem.*, 2004, 4:395-408.
Drontle, et al., "Design a pronucleotide stratagem: lessons from amino acid phosphoramidates of anticancer and antiviral pyrimidines", *Mini Rev. Med. Chem.*, 2004, 4:409-419.
Meyer, et al., "Synthesis of purine nucleoside 3', 5'-cyclic phosphoramidates", *Tetrahedron Lett.*, 1973, 269-272.
Nagyvary, et al., "Studies on neutral esters of cyclic AMP", *Biochem. Biophys. Res. Commun.*, 1973, 55:1072-1077.
Namane, et al., "Improved brain delivery of AZT using a glycosyl phosphotriester prodrug", *J. Med. Chem.*, 1992, 35:3039-3044.
Nargeot, et al., *Natl. Acad. Sci. U.S.A.*, 1983, 80:2395-2399.
Nelson, et al., "The question of chair-twist equilibria for the phosphate rings of nucleoside cyclic 3', 5' monophosphates. $^{1}$HNMR and x-ray crystallographic study of the diastereomers of thymidine phenyl cyclic 3', 5'-monophosphate", *J. Am. Chem. Soc.*, 1987, 109:4058-4064.
Nerbonne, et al., "New photoactivatable cyclic nucleotides produce intracellular jumps in cyclic AMP and cyclic GMP concentrations", *Nature*, 1984, 301:74-76.
Neumann, et al., "Synthesis and transmembrane transport studies by NMR of a glucosyl phospholipid of thymidine", *J. Am. Chem. Soc.*, 1989, 111:4270-4277.
Ohno, et al., "Treatment of myelodysplastic syndromes with orally administered 1-®-D-arabinouranosylcytosine-5' stearylphosphate", *Oncology*, 1991, 48:451-455.
Palomino, et al., "A dihydropyridine carrier system for sustained delivery of 2', 3' dideoxynucleosides to the brain", *J. Med. Chem.*, 1989, 32:622-625.
Piantadosi, et al., "Synthesis and evaluation of novel ether lipid nucleoside conjugates for anti-HIV-1 activity", *J. Med. Chem.*, 1991, 34:1408-1414.
Pompon, et al., "Decomposition pathways of the mono- and bis(pivaloyloxymethyl) esters of azidothymidine-5'-monophosphate in cell extract and in tissue culture medium; an application of the 'on-line ISRP-cleaning HPLC technique", *Antiviral Chem Chemother.*, 1994, 5:91-98.
Postemark, et al., "Cyclic AMP and cyclic GMP", *Annu. Rev. Pharmacol.*, 1974, 14:23-33.
Prisbe, et al., "Synthesis and antiherpes virus activity of phosphate an phosphonate derivatives of 9-[(1, 3-dihydroxy-2-propoxy)methyl] guanine", *J. Med. Chem.*, 1986, 29:671-675.
Pucch, et al., "Intracellular delivery of nucleoside monophosphate through a reductase-mediated activation process", *Antivral Res.*, 1993, 22:155-174.
Robins, et al., "The potential of nucleotide analogs as inhibitors of Retro viruses and tumors", *Pharm. Res.*, 1984, 11-18.
Rosowsky, et al., "Lipophilic 5'-(alkylphosphate) esters of 1-®-D-arabinofuranosylcytosine and its $N^{4}$-acyl and 2.2'-anhydro-3'-O-acyl derivatives as potential prodrugs", *J. Med. Chem.*, 1982, 25:171-178.
Ross, W., "Increased sensitivity of the walker turnout towards aromatic nitrogen mustards carrying basic side chains following glucose pretreatment", *Biochem. Pharm.*, 1961, 8:235-240.
Ryu, et al., "Phospholipid-nucleoside conjugates. 3. Synthesis and preliminary biological evaluation of 1-®-D-arabinofuranosylcytosine 5'-diphosphate [–], 2-diacylglycerols", *J. Med. Chem.*, 1982, 25:1322-1329.
Saffhill, et al., "The degradation of 5-iododeoxyuridine and 5-bromoethoxyuridine by serum from different sources and its consequences for the use of these compounds for incorporation into DNA", *Chem. Biol. Interact.*, 1986, 57:347-355.
Sastry, et al., "Membrane-permeable dideoxyuridine 5'-monophosphate analogue inhibits human immunodeficiency virus infection", *Mol. Pharmacol.*, 1992, 41:441-445.
Shuto, et al., "A facile one-step synthesis of 5' phosphatidylnucleosides by an enzymatic two-phase reaction." *Tetrahedron L4ett.*, 1987, 28:199-202.
Kim et al., *J. Org. Chem.*, 1991, 56:2642-2647.
Nguyen-Trung, et al., *J. Org. Chem.*, 2003, 68:2038-2041.
Holy, et al., *Tetrahedron Lett.*, 1967, 881-884.
Koh, et al., *J. Med. Chem.*, 2005, 48:2867-2875.
Wolff-Kungel, Halazy, *Tetrahedron Lett.*, 1991, 32:6341-6344.
Schinazi et al., Antimicrob. *Agents Chemother.*, 1992, 36:2423-2431.
Schinazi, et al., *Antimicrob. Agents Chemother.*, 1990, 34:1061-1067.
Chou, et al., Adv. *Enzyme Regul.*, 1984, 22:27-55.
Ladner, et al., *Antimicrob. Agents Chemother.*, 1997, 41:1715-1720.
Kao et al., *J. Virol.*, 2000, 74:11121-11128.
Dienstag, J.L., Non-A, non-B hepatitis. I. Recognition, epidemiology, and clinical features. Gastroenterology. Aug. 1983;85(2):439-62.
Greene et al., Protective Groups in Organic Synthesis. John Wiley and Sons, Second Edition, 1991.
Handschumacher et al, Purine and pyrimidine antimetabolites. Cancer Medicine. Ch. XV-1, 3rd Editon, edited by Holland et al. Lea and Febigol, 1993.

(56) References Cited

OTHER PUBLICATIONS

Juodka et al., Synthesis of diribonucleoside phospho-(P?N)-amino acid derivatives. Collect Czech Chem Commun. 1974;39:963-968.

Luethy (Luthy) et al., Mitt Geb Lebensmittelunters Hyg. 1981;72:131-133 (Chem Abstr, 95, 127093).

McGuigan et al., Alkyl hydrogen phosphonate derivatives of the anti-HIV agent AZT may be less toxic than the parent nucleoside analogue. Antiviral Chemistry & Chemotherapy. 1994;5(4):271-277.

Pugaeva et al., [Toxicological assessment and hygienic standardization of ethylene sulfide in the air of industrial plants]. Gig Tr Prof Zabol. Aug. 1969;13(8):47-8.1969 (Chem Abstr, v72, p. 121).

* cited by examiner

2'-FLUORONUCLEOSIDE PHOSPHONATES AS ANTIVIRAL AGENTS

FIELD OF THE INVENTION

This invention is in the area of pharmaceutical chemistry, and in particular, describes 2'-fluoronucleoside phosphonates and methods for their preparation and use.

BACKGROUND OF THE INVENTION

Synthetic nucleosides such as 5-iodouracil and 5-fluorouracil have been used for the treatment of cancer for many years. Since the 1980's, synthetic nucleosides have also been a focus of interest for the treatment of HIV and hepatitis.

In 1981, acquired immune deficiency syndrome (AIDS) was identified as a disease that severely compromises the human immune system, and that almost without exception leads to death. In 1983, the etiological cause of AIDS was determined to be the human immunodeficiency virus (HIV). In 1985, it was reported that the synthetic nucleoside 3'-azido-3'-deoxythymidine (AZT) inhibits the replication of human immunodeficiency virus. Since then, a number of other synthetic nucleosides, including 2',3'-dideoxyinosine (DDI), 2',3'-dideoxycytidine (DDC), and 2',3'-dideoxy-2',3'-didehydrothymidine (D4T), have been proven to be effective against HIV. After cellular phosphorylation to the 5'-triphosphate by cellular kinases, these synthetic nucleosides are incorporated into a growing strand of viral DNA, causing chain termination due to the absence of the 3'-hydroxyl group. They can also inhibit the viral enzyme reverse transcriptase.

The success of various synthetic nucleosides in inhibiting the replication of HIV in vivo or in vitro has led a number of researchers to design and test nucleosides that substitute a heteroatom for the carbon atom at the 3'-position of the nucleoside. European Patent Publication No. 0 337 713 and U.S. Pat. No. 5,041,449, assigned to BioChem Pharma, Inc., disclose 2-substituted-4-substituted-1,3-dioxolanes that exhibit antiviral activity. U.S. Pat. No. 5,047,407 and European Patent Publication No. 0 382 526, also assigned to BioChem Pharma, Inc., disclose that a number of 2-substituted-5-substituted-1,3-oxathiolane nucleosides have antiviral activity, and specifically report that 2-hydroxymethyl-5-(cytosin-1-yl)-1,3-oxathiolane (referred to below as BCH-189) has approximately the same activity against HIV as AZT, with little toxicity.

It has also been disclosed that cis-2-hydroxymethyl-5-(5-fluorocytosin-1-yl)-1,3-oxathiolane ("FTC") has potent HIV activity. Schinazi, et al., "Selective Inhibition of Human Immunodeficiency viruses by Racemates and Enantiomers of cis-5-Fluoro-1-[2-(Hydroxymethyl)-1,3-Oxathiolane-5-yl]-Cytosine" Antimicrobial Agents and Chemotherapy, November 1992, 2423-2431. See also U.S. Pat. Nos. 5,210,085; 5,814,639; and 5,914,331.

Another virus that causes a serious human health problem is the hepatitis B virus (referred to below as "HBV"). HBV is second only to tobacco as a cause of human cancer. The mechanism by which HBV induces cancer is unknown. It is postulated that it may directly trigger tumor development, or indirectly trigger tumor development through chronic inflammation, cirrhosis, and cell regeneration associated with the infection.

After a two to six month incubation period in which the host is unaware of the infection, HBV infection can lead to acute hepatitis and liver damage, that causes abdominal pain, jaundice, and elevated blood levels of certain enzymes. HBV can cause fulminant hepatitis, a rapidly progressive, often fatal form of the disease in which massive sections of the liver are destroyed.

Patients typically recover from acute hepatitis. In some patients, however, high levels of viral antigen persist in the blood for an extended, or indefinite, period, causing a chronic infection. Chronic infections can lead to chronic persistent hepatitis. Patients infected with chronic persistent HBV are most common in developing countries. By mid-1991, there were approximately 225 million chronic carriers of HBV in Asia alone, and worldwide, almost 300 million carriers. Chronic persistent hepatitis can cause fatigue, cirrhosis of the liver, and hepatocellular carcinoma, a primary liver cancer.

In western industrialized countries, high risk groups for HBV infection include those in contact with HBV carriers or their blood samples. The epidemiology of HBV is very similar to that of acquired immune deficiency syndrome, which accounts for why HBV infection is common among patients with AIDS or AIDS related complex. However, HBV is more contagious than HIV.

Both FTC and 3TC exhibit activity against HBV. Furman, et al., "The Anti-Hepatitis B Virus Activities, Cytotoxicities, and Anabolic Profiles of the (−) and (+) Enantiomers of cis-5-Fluoro-1-[2-(Hydroxymethyl)-1,3-oxathiolane-5-yl]-Cytosine" Antimicrobial Agents and Chemotherapy, December 1992, pp. 2686-2692; and Cheng, et al., Journal of Biological Chemistry, Volume 267(20), pp. 13938-13942 (1992). Other compounds that exhibit activity against HBV in humans include Clevudine or CLV (L-FMAU) (Pharmasset, Inc. under license from The University of Georgia Research Foundation and Yale University), and L-dT and L-dC (Idenix Pharmaceuticals, Inc.).

HCV is the major causative agent for post-transfusion and for sporadic non A, non B hepatitis (Alter, H. J. (1990) J. Gastro. Hepatol. 1:78-94; Dienstag, J. L. (1983) Gastro 85:439-462). Despite improved screening, HCV still accounts for at least 25% of the acute viral hepatitis in many countries (Alter, H. J. (1990) supra; Dienstag, J. L. (1983) supra; Alter M. J. et al. (1990a) J.A.M.A. 264:2231-2235; Alter M. J. et al (1992) N. Engl. J. Med. 327:1899-1905; Alter, M. J. et al. (1990b) N. Engl. J. Med. 321:1494-1500). Infection by HCV is insidious in a high proportion of chronically infected (and infectious) carriers who may not experience clinical symptoms for many years. The high rate of progression of acute infection to chronic infection (70-100%) and liver disease (>50%), its world-wide distribution and lack of a vaccine make HCV a significant cause of morbidity and mortality. Currently, there are three types of interferon and a combination of interferon and ribavirin used to treat hepatitis C. Selection of patients for treatment may be determined by biochemical, virologic, and when necessary, liver biopsy findings, rather than presence or absence of symptoms.

Interferon is given by injection, and may have a number of side effects including flu-like symptoms including headaches, fever, fatigue, loss of appetite, nausea, vomiting, depression and thinning of hair. It may also interfere with the production of white blood cells and platelets by depressing the bone marrow. Periodic blood tests are required to monitor blood cells and platelets. Ribavirin can cause sudden, severe anemia, and birth defects so women should avoid pregnancy while taking it and for 6 months following treatment. The severity and type of side effects differ for each individual. Treatment of children with HCV is not currently approved but is under investigation. While 50-60% of patients respond to treatment initially, lasting clearance of the virus occurs in only about 10-40% of patients. Treatment may be prolonged and given a second time to those who relapse after initial treatment. Re-treatment with bioengineered consensus interferon alone results in elimination of the virus in 58% of patients treated for one year. Side effects occur but the medication is usually well tolerated. Combined therapy (interferon and ribavirin) shows elimination of the virus in 47% after 6 months of therapy. Side effects from both drugs may be prominent.

A tumor is an unregulated, disorganized proliferation of cell growth. A tumor is malignant, or cancerous, if it has the properties of invasiveness and metastasis. Invasiveness refers to the tendency of a tumor to enter surrounding tissue, breaking through the basal laminas that define the boundaries of the tissues, thereby often entering the body's circulatory system. Metastasis refers to the tendency of a tumor to migrate to other areas of the body and establish areas of proliferation away from the site of initial appearance.

Cancer is now the second leading cause of death in the United States. Over 8,000,000 persons in the United States have been diagnosed with cancer, with 1,208,000 new diagnoses expected in 1994. Over 500,000 people die annually from the disease in this country.

Cancer is not fully understood on the molecular level. It is known that exposure of a cell to a carcinogen such as certain viruses, certain chemicals, or radiation, leads to DNA alteration that inactivates a "suppressive" gene or activates an "oncogene." Suppressive genes are growth regulatory genes, which upon mutation, can no longer control cell growth. Oncogenes are initially normal genes (called prooncogenes) that by mutation or altered context of expression become transforming genes. The products of transforming genes cause inappropriate cell growth. More than twenty different normal cellular genes can become oncongenes by genetic alteration. Transformed cells differ from normal cells in many ways, including cell morphology, cell-to-cell interactions, membrane content, cytoskeletal structure, protein secretion, gene expression and mortality (transformed cells can grow indefinitely).

All of the various cell types of the body can be transformed into benign or malignant tumor cells. The most frequent tumor site is lung, followed by colorectal, breast, prostate, bladder, pancreas and then ovary. Other prevalent types of cancer include leukemia, central nervous system cancers, including brain cancer, melanoma, lymphoma, erythroleukemia, uterine cancer, and head and neck cancer.

Cancer is now primarily treated with one or a combination of three means of therapies: surgery, radiation and chemotherapy. Surgery involves the bulk removal of diseased tissue. While surgery is sometimes effective in removing tumors located at certain sites, for example, in the breast, colon and skin, it cannot be used in the treatment of tumors located in other areas, such as the backbone, or in the treatment of disseminated neoplastic conditions such as leukemia.

Chemotherapy involves the disruption of cell replication or cell metabolism. It is used most often in the treatment of leukemia, as well as breast, lung, and testicular cancer.

There are five major classes of chemotherapeutic agents currently in use for the treatment of cancer: natural products and their derivatives; anthacyclines; alkylating agents; antiproliferatives (also called antimetabolites); and hormonal agents. Chemotherapeutic agents are often referred to as antineoplastic agents.

The alkylating agents are believed to act by alkylating and cross-linking guanine and possibly other bases in DNA, arresting cell division. Typical alkylating agents include nitrogen mustards, ethyleneimine compounds, alkyl sulfates, cisplatin and various nitrosoureas. A disadvantage with these compounds is that they not only attach malignant cells, but also other cells which are naturally dividing, such as those of bone marrow, skin, gastrointestinal mucosa, and fetal tissue.

Antimetabolites are typically reversible or irreversible enzyme inhibitors, or compounds that otherwise interfere with the replication, translation or transcription of nucleic acids.

Several synthetic nucleosides have been identified that exhibit anticancer activity. A well known nucleoside derivative with strong anticancer activity is 5-fluorouracil. 5-Fluorouracil has been used clinically in the treatment of malignant tumors, including, for example, carcinomas, sarcomas, skin cancer, cancer of the digestive organs, and breast cancer. 5-Fluorouracil, however, causes serious adverse reactions such as nausea, alopecia, diarrhea, stomatitis, leukocytic thrombocytopenia, anorexia, pigmentation and edema. Derivatives of 5-fluorouracil with anti-cancer activity have been described in U.S. Pat. No. 4,336,381, and in Japanese patent publication Nos. 50-50383, 50-50384, 50-64281, 51-146482, and 53-84981.

U.S. Pat. No. 4,000,137 discloses that the peroxidate oxidation product of inosine, adenosine or cytidine with methanol or ethanol has activity against lymphocytic leukemia.

Cytosine arabinoside (also referred to as Cytarabin, araC, and Cytosar) is a nucleoside analog of deoxycytidine that was first synthesized in 1950 and introduced into clinical medicine in 1963. It is currently an important drug in the treatment of acute myeloid leukemia. It is also active against acute lymphocytic leukemia, and to a lesser extent, is useful in chronic myelocytic leukemia and non-Hodgkin's lymphoma. The primary action of araC is inhibition of nuclear DNA synthesis. Handschumacher, R. and Cheng, Y., "Purine and Pyrimidine Antimetabolites" Cancer Medicine, Chapter XV-1, 3rd Edition, Edited by J. Holland, et al., Lea and Febigol, publishers.

5-Azacytidine is a cytidine analog that is primarily used in the treatment of acute myelocytic leukemia and myelodysplastic syndrome.

2-Fluoroadenosine-5'-phosphate (Fludara, also referred to as FaraA) is one of the most active agents in the treatment of chronic lymphocytic leukemia. The compound acts by inhibiting DNA synthesis. Treatment of cells with F-araA is associated with the accumulation of cells at the G1/S phase boundary and in S phase; thus, it is a cell cycle S phase-specific drug. Incorporation of the active metabolite, F-araATP, retards DNA chain elongation. F-araA is also a potent inhibitor of ribonucleotide reductase, the key enzyme responsible for the formation of dATP.

2-Chlorodeoxyadenosine is useful in the treatment of low grade B-cell neoplasms such as chronic lymphocytic leukemia, non-Hodgkins' lymphoma, and hairy-cell leukemia.

In designing new nucleosides, there have been a number of attempts to incorporate a fluoro substituent into the carbohydrate ring of the nucleoside. Fluorine has been suggested as a substituent because it might serve as an isopolar and isosteric mimic of a hydroxyl group as the C—F bond length (1.35 Å) is so similar to the C—O bond length (1.43 Å) and because fluorine is a hydrogen bond acceptor. Fluorine is capable of producing significant electronic changes in a molecule with minimal steric perturbation. The substitution of fluorine for another group in a molecule can cause changes in substrate metabolism because of the high strength of the C—F bond (116 kcal/mol vs. C—H=100 kcal/mol).

A number of references have reported the synthesis and use of 2'-arabinofluoro-nucleosides (i.e., nucleosides in which a 2'-fluoro group is in the "up"-configuration). There have been several reports of 2-fluoro-β-D-arabinofuranosyl nucleosides that exhibit activity against hepatitis B and herpes. See, for example, U.S. Pat. No. 4,666,892 to Fox, et al.; U.S. Pat. No. 4,211,773 to Lopez, et al; Su, et al., Nucleosides. 136. Synthesis and Antiviral Effects of Several 1-(2-Deoxy-2-fluoro-β-D-arabinofuranosyl)-5-alkyluracils. Some Structure-Activity Relationships, J. Med. Chem., 1986, 29, 151-154; Borthwick, et al., Synthesis and Enzymatic Resolution of Carbocyclic 2'-Ara-fluoro-Guanosine: A Potent New Anti-Herpetic Agent, J. Chem. Soc., Chem. Commun, 1988; Wantanabe, et al., Synthesis and Anti-HIV Activity of 2'-"Up"-Fluoro Analogues of Active Anti-Aids Nucleosides 3'-Azido-3'-deoxythymidine (AZT) and 2',3'-deoxythymidine (AZT) and 2',3'-dideoxycytidine (DDC), J. Med. Chem. 1990, 33, 2145-2150; Martin, et al., Synthesis and Antiviral Activity of Monofluoro and Difluoro Analogues of Pyrimidine Deoxyribonucleosides against Human Immunodeficiency Virus (HIV-1), J. Med. Chem. 1990, 33, 2137-2145; Sterzycki, et al., Synthesis and Anti-HIV Activity of Several 2'-Fluoro-Containing Pyrimidine Nucleosides, J. Med. Chem. 1990, as well as EPA 0 316 017 also filed by Sterzycki, et al.; and Montgomery, et al., 9-(2-Deoxy-2-fluoro-β-D-arabinofuranosyl)-guanine: A Metabolically Stable Cytotoxic Analogue of 2'-Deoxyguanosine. U.S. Pat. No. 5,246,924 discloses a method for treating a hepatitis infection that includes the administration of 1-(2'-deoxy-2'-fluoro-β-D-arabinofuranosyl)-3-ethyluracil), also referred to as "FEAU." U.S. Pat. No. 5,034,518 discloses 2-fluoro-9-(2-deoxy-2-fluoro-β-D-arabino-furanosyl)adenine nucleosides which exhibit anticancer activity by altering the metabolism of adenine nucleosides by reducing the ability of the compound to serve as a substrate for adenosine. EPA 0 292 023 discloses that certain β-D-2'-fluoroarabinonucleosides are active against viral infections.

U.S. Pat. No. 5,128,458 discloses β-D-2',3'-dideoxy-4'-thioribonucleosides as antiviral agents. U.S. Pat. No. 5,446,029 discloses that 2',3'-dideoxy-3'-fluoro-nucleosides have anti-hepatitis activity.

European Patent Publication No. 0 409 227 A2 discloses certain 3'-substituted β-D-pyrimidine and purine nucleosides for the treatment of hepatitis B.

It has also been disclosed that L-FMAU (2'-fluoro-5-methyl-β-L-arabinofuranosyl-uracil) is a potent anti-HBV and anti-EBV agent. See Chu, et al., Use of 2'-Fluoro-5-methyl-β-L-arabinofuranosyluracil as a Novel Antiviral Agent for Hepatitis B Virus and Epstein-Barr Virus; Antimicrobial Agents and Chemotherapy, April 1995, 979-981; Balakrishna, et al., Inhibition of Hepatitis B Virus by a Novel L-Nucleoside, 2'-Fluoro-5-Methyl-β-L-arabinofuranosyl Uracil, Antimicrobial Agents and Chemotherapy, February 1996, 380-356; U.S. Pat. Nos. 5,587,362; 5,567,688; and 5,565,438.

U.S. Pat. Nos. 5,426,183 and 5,424,416 disclose processes for preparing 2'-deoxy-2',2'-difluoronucleosides and 2'-deoxy-2'-fluoro nucleosides. See also Kinetic Studies of 2',2'-difluorodeoxycytidine (Gemcitabine) with Purified Human Deoxycytidine Kinase and Cytidine Deaminase, Bio-Chemical Pharmacology, Vol. 45 (No. 9) pages 4857-4861, 1993.

U.S. Pat. No. 5,446,029 to Eriksson, et al., discloses that certain 2',3'-dideoxy-3'-fluoronucleosides have hepatitis B activity. U.S. Pat. No. 5,128,458 discloses certain 2',3'-dideoxy-4'-thioribonucleosides wherein the 3'-substituent is H, azide or fluoro. WO 94/14831 discloses certain 3'-fluoro-dihydropyrimidine nucleosides. WO 92/08727 discloses β-L-2'-deoxy-3'-fluoro-5-substituted uridine nucleosides for the treatment of herpes simplex 1 and 2.

European Patent Publication No. 0 352 248 discloses a broad genus of L-ribofuranosyl purine nucleosides for the treatment of HIV, herpes, and hepatitis. While certain 2'-fluorinated purine nucleosides fall within the broad genus, there is no information given in the specification on how to make these compounds in the specification, and they are not among specifically disclosed or the preferred list of nucleosides in the specification. The specification does disclose how to make 3'-ribofuranosyl fluorinated nucleosides. A similar specification is found in WO 88/09001, filed by Aktiebolaget Astra.

European Patent Publication No. 0 357 571 discloses a broad group of β-D and 〈-D pyrimidine nucleosides for the treatment of AIDS which among the broad class generically includes nucleosides that can be substituted in the 2' or 3'-position with a fluorine group. Among this broad class, however, there is no specific disclosure of 2'-fluorinated nucleosides or a method for their production.

European Patent Publication No. 0 463 470 discloses a process for the preparation of (5S)-3-fluoro-tetrahydro-5-[(hydroxy)methyl]-2-(3H)-furanone, a known intermediate in the manufacture of 2'-fluoro-2',3'-dideoxynucleosides such as 2'-fluoro-2', 3'-dideoxycytidine.

U.S. Pat. Nos. 5,817,799 and 5,336,764 disclose β-D-2'-fluoroarabinofuranosyl nucleosides, and a method for their production, which are intermediates in the synthesis of 2',3'-dideoxy-2'-fluoroarabinosyl nucleosides.

U.S. Pat. No. 4,625,020 discloses a method of producing 1-halo-2-deoxy-2-fluoroarabinofuranosyl derivatives bearing protective ester groups from 1,3,5-tri-O-acyl-ribofuranose.

U.S. Pat. No. 6,348,587 and International Publication No. WO 99/43691 disclose certain 2'-fluoronucleosides, including certain 2'-fluoro-2',3'-dideoxy-2',3'-didehydro-4'-((S, $CH_2$ or CHF))-nucleosides, and their uses for the treatment of HIV, hepatitis (B or C), or proliferative conditions.

International Publication Nos. WO 01/90121 and WO 01/92282 disclose a wide variety of nucleosides for the treatment of HCV and flaviviruses and pestiviruses, respectively, including certain 2'-halo-2',3'-dideoxy-2',3'-didehydro-4'-(O, S, $SO_2$ or $CH_2$)-nucleosides.

International Publication Nos. WO 04/02422, WO 04/02999, and WO 04/03000 disclose 2'-C-methyl ribonucleosides for the treatment of HCV and flaviviruses and pestiviruses.

International Publication No. WO 05/003147 discloses 2'-deoxy-2'-fluoro-2'-methyl ribonucleosides for the treatment of HCV and flaviviruses and pestiviruses, respectively.

A nucleoside 5'-phosphonate is essentially a nucleoside monophosphate analogue. However, a phosphonate has the advantage over its phosphate counterpart of being metabolically stable, as its phosphorus-carbon bond is not susceptible to phosphatase hydrolysis. More importantly, the presence of a 5'-phosphonate allows the first phosphorylation step required for nucleoside activation to be skipped, therefore bypassing this inefficient and often rate-limiting step in the conversion to 5'-triphosphate. Like a nucleoside monophosphate, a nucleoside phosphonate can be further phosphorylated by cellular nucleotide kinases. The concept of nucleoside phosphonate has been applied to design chain terminators for anti-HIV chemotherapy and proved to be valid. 9-(2-Phosphonylmethoxypropyl)adenine (PMPA) and 9-(2 phosphonylmethoxyethyl)adenine (PMEA) are two effective and potent nucleoside phosphonate chain terminators for HIV reverse transcriptase (RT). See De Clercq, et al., A novel selective broad-spectrum anti-DNA virus agent, *Nature* 1986, 323, 464-467; Balzarini, et al., Marked in vivo anti-retrovirus activity of 9-(2-phosphonylmethoxyethyl)-adenine, a selective anti-human immunodeficiency virus agent, *Proc. Natl. Acad. Sci. U.S.A.* 1989, 86, 332-336; Balzarini, et al., Differential anti-herpes virus and anti-retrovirus effects of the (S) and (R) enantiomers of acyclic nucleoside phosphonates: Potent and selective in vitro and in vivo anti-retrovirus activities of (R)-9-(2-phosphonomethoxypropyl)-2,6-diaminopurine, *Antimicrob. Agents Chemother.* 1993, 37, 332-338.

European Patent No. 398,231, U.S. Pat. No. 5,886,179, and International Publication No. WO 04/096233 disclose a wide variety of nucleoside phosphonates, and their uses as antitumor and antiviral agents.

U.S. Patent Publication Nos. 05/2155513, 04/023921, and International Publication Nos. WO 04/096286, WO 04/096235 disclose a wide variety of nucleoside phosphonates, and their uses for the treatment of HIV, hepatitis (B or C), or proliferative conditions.

European Patent Publication No. 0369409 discloses certain carbocyclic nucleoside phosphonates, including ribo, deoxyribo, and halogen (excluding fluorine) substituted carbocyclic nucleoside phosphonates, and their uses for the treatment of tumor and viral infections.

In light of the fact that acquired immune deficiency syndrome, AIDS-related complex, hepatitis B virus and hepatitis C virus have reached epidemic levels worldwide, and have tragic effects on the infected patient, there remains a strong need to provide new effective pharmaceutical agents to treat these diseases that have low toxicity to the host. Further, there is a need to provide new antiproliferative agents.

Therefore, it is an object of the present invention to provide a method and composition for the treatment of human patients or other host animals infected with HIV.

It is another object of the present invention to provide a method and composition for the treatment of human patients infected with hepatitis B or C.

It is a further object of the present invention to provide new antiproliferative agents.

It is still another object of the present invention to provide a new process for the preparation of 2'-fluoronucleoside phosphonates of the present invention.

SUMMARY OF THE INVENTION

The present invention includes β-D and β-L-2'-fluoronucleoside phosphonates, pharmaceutical compositions comprising such compounds, as well as methods to treat or prevent an HIV infection, HBV infection or abnormal cellular proliferation comprising administering said compounds or compositions. In addition, the present invention includes the process for the preparation of such compounds, and the related β-D and β-L-2'-fluoronucleoside phosphonates.

In one embodiment, the compound of the invention is a 2'-fluoronucleoside phosphonate of the general formula (I)-(IV):

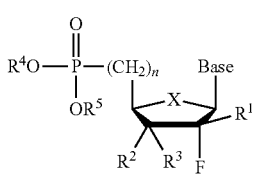

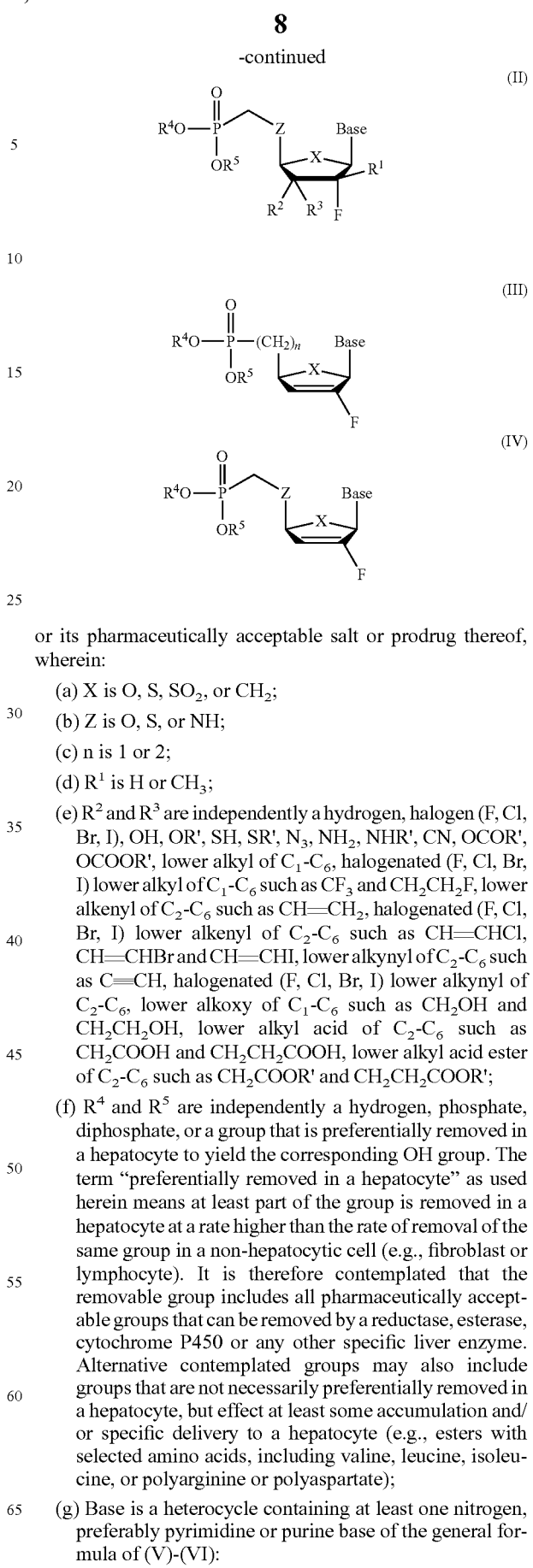

or its pharmaceutically acceptable salt or prodrug thereof, wherein:

(a) X is O, S, $SO_2$, or $CH_2$;

(b) Z is O, S, or NH;

(c) n is 1 or 2;

(d) $R^1$ is H or $CH_3$;

(e) $R^2$ and $R^3$ are independently a hydrogen, halogen (F, Cl, Br, I), OH, OR', SH, SR', $N_3$, $NH_2$, NHR', CN, OCOR', OCOOR', lower alkyl of $C_1$-$C_6$, halogenated (F, Cl, Br, I) lower alkyl of $C_1$-$C_6$ such as $CF_3$ and $CH_2CH_2F$, lower alkenyl of $C_2$-$C_6$ such as CH=$CH_2$, halogenated (F, Cl, Br, I) lower alkenyl of $C_2$-$C_6$ such as CH=CHCl, CH=CHBr and CH=CHI, lower alkynyl of $C_2$-$C_6$ such as C≡CH, halogenated (F, Cl, Br, I) lower alkynyl of $C_2$-$C_6$, lower alkoxy of $C_1$-$C_6$ such as $CH_2OH$ and $CH_2CH_2OH$, lower alkyl acid of $C_2$-$C_6$ such as $CH_2COOH$ and $CH_2CH_2COOH$, lower alkyl acid ester of $C_2$-$C_6$ such as $CH_2COOR'$ and $CH_2CH_2COOR'$;

(f) $R^4$ and $R^5$ are independently a hydrogen, phosphate, diphosphate, or a group that is preferentially removed in a hepatocyte to yield the corresponding OH group. The term "preferentially removed in a hepatocyte" as used herein means at least part of the group is removed in a hepatocyte at a rate higher than the rate of removal of the same group in a non-hepatocytic cell (e.g., fibroblast or lymphocyte). It is therefore contemplated that the removable group includes all pharmaceutically acceptable groups that can be removed by a reductase, esterase, cytochrome P450 or any other specific liver enzyme. Alternative contemplated groups may also include groups that are not necessarily preferentially removed in a hepatocyte, but effect at least some accumulation and/or specific delivery to a hepatocyte (e.g., esters with selected amino acids, including valine, leucine, isoleucine, or polyarginine or polyaspartate);

(g) Base is a heterocycle containing at least one nitrogen, preferably pyrimidine or purine base of the general formula of (V)-(VI):

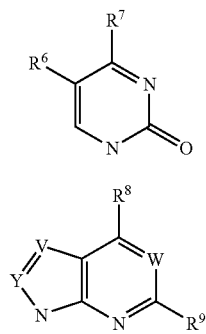

or its pharmaceutically acceptable salt or prodrug thereof, wherein:

(i) W, Y and V are independently N, CH, or $CR^{10}$;

(ii) $R^6$ is a hydrogen, halogen (F, Cl, Br, I), OH, OR', SH, SR', $NH_2$, NHR', $NR'_2$, COOH, COOR', $CONH_2$, CONHR', $CONR'_2$, $CH=CHCO_2H$, $CH=CHCO_2R'$, lower alkyl of $C_1$-$C_6$, halogenated (F, Cl, Br, I) lower alkyl of $C_1$-$C_6$ such as $CF_3$ and $CH_2CH_2F$, lower alkenyl of $C_2$-$C_6$ such as $CH=CH_2$, halogenated (F, Cl, Br, I) lower alkenyl of $C_2$-$C_6$ such as $CH=CHCl$, $CH=CHBr$ and $CH=CHI$, lower alkynyl of $C_2$-$C_6$ such as $C\equiv CH$, halogenated (F, Cl, Br, I) lower alkynyl of $C_2$-$C_6$, lower alkoxy of $C_1$-$C_6$ such as $CH_2OH$ and $CH_2CH_2OH$, lower alkyl acid of $C_2$-$C_6$ such as $CH_2COOH$ and $CH_2CH_2COOH$, lower alkyl acid ester of $C_2$-$C_6$ such as $CH_2COOR'$ and $CH_2CH_2COOR'$;

(iii) $R^7$, $R^8$ and $R^9$ are independently a hydrogen, halogen (F, Cl, Br, I), OH, OR', SH, SR', $NH_2$, NHR', $NR'_2$, OCOR', OCOOR', NHCOR', NHCOOR';

(iv) $R^{10}$ is a halogen, alkyl, ary, acyl;

(h) each R' is independently a hydrogen, lower alkyl of $C_1$-$C_6$ or lower cycloalkyl of $C_1$-$C_6$;

In a particular embodiment of the present invention, a β-D 2'-fluoronucleoside phosphonate of the formula:

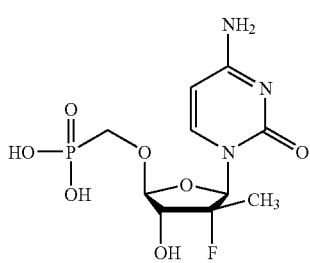

its β-L enantiomer, or its pharmaceutically acceptable salt or prodrug thereof, is provided for the treatment or prophylaxis of a viral infection, including HIV, HBV, and HCV, or a disease associated with abnormal cellular proliferation, and in particular a malignant tumor.

In another particular embodiment of the present invention, a β-D 2'-fluoronucleoside phosphonate of the formula:

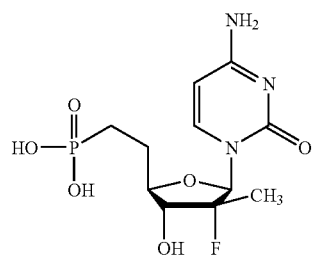

its β-L enantiomer, or its pharmaceutically acceptable salt or prodrug thereof, is provided for the treatment or prophylaxis of a viral infection, including HIV, HBV, and HCV, or a disease associated with abnormal cellular proliferation, and in particular a malignant tumor.

In yet another particular embodiment of the present invention, a β-D 2'-fluoronucleoside phosphonate of the formula:

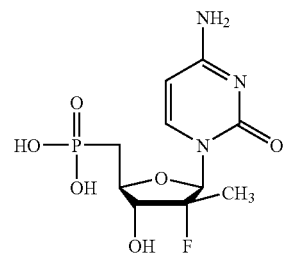

its β-L enantiomer, or its pharmaceutically acceptable salt or prodrug thereof, is provided for the treatment or prophylaxis of a viral infection, including HIV, HBV, and HCV, or a disease associated with abnormal cellular proliferation, and in particular a malignant tumor.

In yet another particular embodiment of the present invention, a β-D 2'-fluoronucleoside phosphonate of the formula:

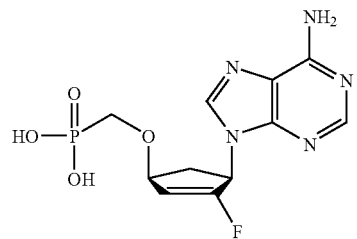 [SMILES: Nc1ncnc2c1ncn2[C@@H]1C[C@H](CCP(=O)(O)O)C=C1F]

its β-L enantiomer, or its pharmaceutically acceptable salt or prodrug thereof, is provided for the treatment or prophylaxis of a viral infection, including HIV, HBV, and HCV, or a disease associated with abnormal cellular proliferation, and in particular a malignant tumor.

In yet another particular embodiment of the present invention, a β-D 2'-fluoronucleoside phosphonate of the formula:

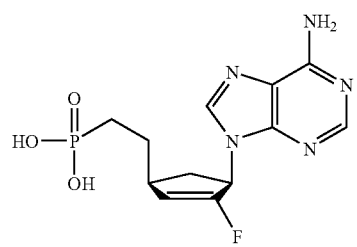

its β-L enantiomer, or its pharmaceutically acceptable salt or prodrug thereof, is provided for the treatment or prophylaxis of a viral infection, including HIV, HBV, and HCV, or a disease associated with abnormal cellular proliferation, and in particular a malignant tumor.

In yet another particular embodiment of the present invention, a β-D 2'-fluoronucleoside phosphonate of the formula:

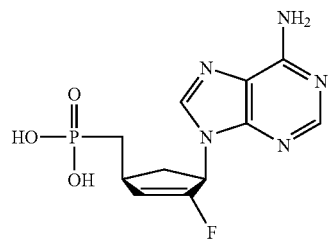 [SMILES: Nc1ncnc2c1ncn2[C@@H]1C[C@H](CP(=O)(O)O)C=C1F]

its β-L enantiomer, or its pharmaceutically acceptable salt or prodrug thereof, is provided for the treatment or prophylaxis of a viral infection, including HIV, HBV, and HCV, or a disease associated with abnormal cellular proliferation, and in particular a malignant tumor.

In yet another particular embodiment of the present invention, a β-D 2'-fluoronucleoside phosphonate of the formula:

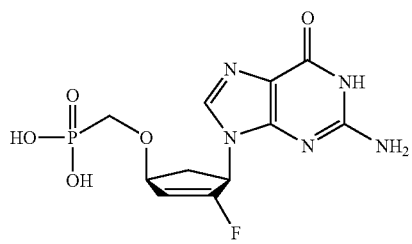

its β-L enantiomer, or its pharmaceutically acceptable salt or prodrug thereof, is provided for the treatment or prophylaxis of a viral infection, including HIV, HBV, and HCV, or a disease associated with abnormal cellular proliferation, and in particular a malignant tumor.

In yet another particular embodiment of the present invention, a β-D 2'-fluoronucleoside phosphonate of the formula:

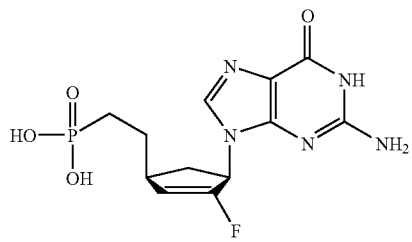 [SMILES: Nc1nc2c(ncn2[C@@H]2C[C@H](CCP(=O)(O)O)C=C2F)c(=O)[nH]1]

its β-L enantiomer, or its pharmaceutically acceptable salt or prodrug thereof, is provided for the treatment or prophylaxis of a viral infection, including HIV, HBV, and HCV, or a disease associated with abnormal cellular proliferation, and in particular a malignant tumor.

In yet another particular embodiment of the present invention, a β-D 2'-fluoronucleoside phosphonate of the formula:

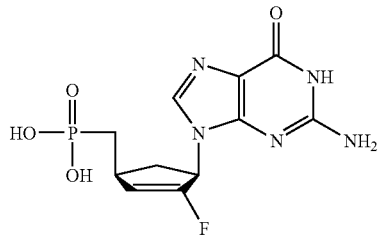 [SMILES: Nc1nc2c(ncn2[C@@H]2C[C@H](CP(=O)(O)O)C=C2F)c(=O)[nH]1]

its β-L enantiomer, or its pharmaceutically acceptable salt or prodrug thereof, is provided for the treatment or prophylaxis of a viral infection, including HIV, HBV, and HCV, or a disease associated with abnormal cellular proliferation, and in particular a malignant tumor.

In one embodiment of the invention, the 2'-fluoronucleoside phosphonate of the invention is the isolated β-D or β-L isomer. In another embodiment of the invention, the 2'-fluoronucleoside phosphonates are enantiomerically enriched. In yet another embodiment of the invention, the 2'-fluoronucleoside phosphonate is in a enantiomeric mixture in which the desired enantiomer is at least 95%, 98% or 99% free of its enantiomer.

In another embodiment, the 2'-fluoronucleoside phosphonate has an $EC_{50}$ (effective concentration to achieve 50% inhibition) when tested in an appropriate cell-based assay, of less than 15 micromolar, and more particularly, less than 10 or 5 micromolar. In a preferred embodiment, the nucleoside is enantiomerically enriched.

In one embodiment of the present invention, the compounds of the formula (I)-(IV) are in the β-D configuration. In an alternate embodiment of the present invention, the compounds of formula (I)-(IV) are in the β-L configuration.

The 2'-fluoronucleoside phosphonates depicted above are in the β-D configuration, however, it should be understood that the 2'-fluoronucleoside phosphonates can be either in the β-L or β-D configuration.

The 2'-fluoronucleosides of the present invention are biologically active molecules that are useful in the treatment or prophylaxis of viral infections, and in particular an human immunodeficiency virus (HIV) and/or hepatitis B virus (HBV) infection. The compounds are also useful for the treatment of abnormal cellular proliferation, including tumors and cancer. In another embodiment of the present invention, any of the active compounds are useful in the treatment of HCV. One can easily determine the spectrum of activity by evaluating the compound in the assays described herein or with another confirmatory assay.

For instance, in one embodiment the efficacy of the antiviral compound is measured according to the concentration of compound necessary to reduce the plaque number of the virus in vitro, according to methods set forth more particularly herein, by 50% (i.e. the compound's $EC_{50}$). In preferred embodiments the compound exhibits an $EC_{50}$ of less than 15 or preferably, less than 10 micromolar in vitro.

In another embodiment, for the treatment or prophylaxis of a viral infection, and in particular an HIV or HBV infection, in a host, the active compound or its derivative or salt can be administered in combination or alternation with another antiviral agent, such as an anti-HIV agent or anti-hepatitis agent, including those of the formula above. Alternatively, for the treatment of abnormal cellular proliferation, such as tumors and cancer, in a host, the active compound or its derivative or salt can be administered in combination or alternation with another antiproliferative agent, such as an anti-neoplastic agent, including those of the formula above. In general, in combination therapy, effective dosages of two or more agents are administered together, whereas during alternation therapy, an effective dosage of each agent is administered serially. The dosages will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

Nonlimiting examples of antiviral agents that can be used in combination with the compounds disclosed herein include 2-hydroxymethyl-5-(5-fluorocytosin-1-yl)-1,3-oxathiolane (FTC); the (−)-enantiomer of 2-hydroxymethyl-5(cytosin-1-yl)-1,3-oxathiolane (3TC); carbovir, acyclovir, interferon, famciclovir, penciclovir, AZT, DDI, DDC, D4T, abacavir, L-(−)-FMAU, L-dT, β-D-2′-C-methylcytidine, L-DDA phosphate prodrugs, and β-D-dioxolane nucleosides such as β-D-dioxolanyl-guanine (DG), β-D-dioxolanyl-2,6-diaminopurine (DAPD), and β-D-dioxolanyl-6-chloropurine (ACP), non-nucleoside room temperature inhibitors such as nevirapine, MKC-442, DMP-266 (sustiva) and also protease inhibitors such as indinavir, saquinavir, DMP-450 and others.

The compounds can also be used to treat equine infectious anemia virus (EIAV), feline immunodeficiency virus, and simian immunodeficiency virus. (Wang, S., Montelaro, R., Schinazi, R. F., Jagerski, B., and Mellors, J. W.: "Activity of nucleoside and non-nucleoside reverse transcriptase inhibitors (NNRTI) against equine infectious anemia virus (EIAV) ." *First National Conference on Human Retro viruses and Related Infections*, Washington, D.C., Dec. 12-16, 1993; Sellon D. C., "Equine Infectious Anemia," *Vet. Clin. North Am. Equine Pract. United States*, 9: 321-336, 1993; Philpott, M. S., Ebner, J. P., Hoover, E. A., "Evaluation of 9-(2-phosphonylmethoxyethyl)adenine therapy for feline immunodeficiency virus using a quantitative polymerase chain reaction," *Vet. Immunol. Immunopathol.* 35:155166, 1992.)

The present invention also provides a pharmaceutical composition for the treatment and/or prophylaxis of a viral infection, and in particular a HBV or HIV infection, in a host, preferably a human, comprising an effective amount of an active compound of the present invention, optionally in a pharmaceutically acceptable carrier.

The present invention also provides a pharmaceutical composition for the treatment and/or prophylaxis of an abnormal cellular proliferation, such as tumors and cancer, in a host, preferably a human, comprising an effective amount of an active compound of the present invention, optionally in a pharmaceutically acceptable carrier.

The present invention also provides a pharmaceutical composition for the treatment and/or prophylaxis of a viral infection, and in particular a HBV or HIV infection, in a host, preferably a human, comprising an effective amount of an active compound of the present invention, in combination with one or more other effective antiviral agent, and in particular an anti-HBV or anti-HIV agent, optionally in a pharmaceutically acceptable carrier.

The present invention also provides a pharmaceutical composition for the treatment and/or prophylaxis of an abnormal cellular proliferation, such as tumors and cancer, in a host, preferably a human, comprising an effective amount of an active compound of the present invention, in combination with one or more other effective antiproliferative agent, such as an antineoplastic agent, optionally in a pharmaceutically acceptable carrier.

The present invention also provides a method for the treatment and/or prophylaxis of a viral infection, and in particular a HBV or HIV infection, in a host, preferably a human, comprising administering to the host an effective amount of an active compound of the present invention, optionally in a pharmaceutically acceptable carrier.

The present invention also provides a method for the treatment and/or prophylaxis of an abnormal cellular proliferation, such as tumors and cancer, in a host, preferably a human, comprising administering to the host an effective amount of an active compound of the present invention, optionally in a pharmaceutically acceptable carrier.

The present invention also provides a method for the treatment and/or prophylaxis of a viral infection, and in particular a HBV or HIV infection, in a host, preferably a human, comprising administering to the host an effective amount of an active compound of the present invention, in combination and/or alternation with one or more other effective antiviral agent, and in particular an anti-HBV or anti-HIV agent, optionally in a pharmaceutically acceptable carrier.

The present invention also provides a method for the treatment and/or prophylaxis of an abnormal cellular proliferation, such as tumors and cancer, in a host, preferably a human, comprising administering to the host an effective amount of an active compound of the present invention, in combination and/or alternation with one or more other effective antiproliferative agent, such as an antineoplastic agent, optionally in a pharmaceutically acceptable carrier.

The present invention also provides a use of an active compound of the present invention, optionally in a pharmaceutically acceptable carrier, for the treatment and/or prophylaxis of a viral infection, and in particular a HBV or HIV infection, in a host, preferably a human.

The present invention also provides a use of an active compound of the present invention, optionally in a pharmaceutically acceptable carrier, for the treatment and/or prophylaxis of an abnormal cellular proliferation, such as tumors and cancer, in a host, preferably a human.

The present invention also provides a use of an active compound of the present invention, in combination and/or alternation with one or more other effective antiviral agent, and in particular an anti-HBV or anti-HIV agent, optionally in a pharmaceutically acceptable carrier, for the treatment and/or prophylaxis of a viral infection, and in particular a HBV or HIV infection, in a host, preferably a human.

The present invention also provides a use of an active compound of the present invention, in combination and/or alternation with one or more other effective antiproliferative agent, such as an antineoplastic agent, optionally in a pharmaceutically acceptable carrier, for the treatment and/or prophylaxis of an abnormal cellular proliferation, such as tumors and cancer, in a host, preferably a human.

The present invention also provides a use of an active compound of the present invention, optionally in a pharmaceutically acceptable carrier, in the manufacture of a medicament for the treatment and/or prophylaxis of a viral infection, and in particular a HBV or HIV infection, in a host, preferably a human.

The present invention also provides a use of an active compound of the present invention, optionally in a pharmaceutically acceptable carrier, in the manufacture of a medicament for the treatment and/or prophylaxis of an abnormal cellular proliferation, such as tumors and cancer, in a host, preferably a human.

The present invention also provides a use of an active compound of the present invention, in combination and/or alternation with one or more other effective antiviral agent, and in particular an anti-HBV or anti-HIV agent, optionally in a pharmaceutically acceptable carrier, in the manufacture of a medicament for the treatment and/or prophylaxis of a viral infection, and in particular a HBV or HIV infection, in a host, preferably a human.

The present invention also provides a use of an active compound of the present invention, in combination and/or alternation with one or more other effective antiviral agent, and in particular an anti-HCV agent, optionally in a pharmaceutically acceptable carrier, in the manufacture of a medicament for the treatment and/or prophylaxis of a viral infection, and in particular a HCV infection, in a host, preferably a human.

The present invention also provides a use of an active compound of the present invention, in combination and/or alternation with one or more other effective antiproliferative agent, such as an antineoplastic agent, optionally in a pharmaceutically acceptable carrier, in the manufacture of a medicament for the treatment and/or prophylaxis of an abnormal cellular proliferation, such as tumors and cancer, in a host, preferably a human.

The invention also provides synthetic methods useful for preparing the compounds of the invention, as well as intermediates disclosed herein that are useful in the preparation of the compounds of the present invention.

BRIEF DESCRIPTION OF THE SCHEMES

Scheme 1 is a nonlimiting illustrative example of the synthesis of 2'-deoxy-2'-fluoronucleoside phosphonates II ($R^1$=H, X=O, S), according to the present invention.

Scheme 2 is a non-limiting illustrative example of the synthesis of carbocyclic 2'-fluoronucleoside phosphonates II ($R^1$=H, X=$CH_2$), according to the present invention.

Scheme 3 is a non-limiting illustrative example of the synthesis of 2',3'-didehydro-2',3'-dideoxy-2'-fluoronucleoside phosphonates Iv (X=O, S), according to the present invention.

Scheme 4 is a non-limiting illustrative example of the synthesis of carbocyclic 2',3'-dideoxy-2',3'-didehydro-2'-fluoronucleoside phosphonates IV (X=$CH_2$), according to the present invention.

Scheme 5 is a non-limiting illustrative example of the synthesis of 2'-deoxy-2'-methyl-2'-fluoronucleoside phosphonates II ($R^1$=$CH_3$, X=O, S), according to the present invention.

Scheme 6 is a non-limiting illustrative example of the synthesis of carbocyclic 2'-deoxy-2'-methyl-2'-fluoronucleoside phosphonates II (X=$CH_2$, $R^1$=$CH_3$), according to the present invention.

Scheme 7 are non-limiting illustrative examples of the synthesis of 2'-deoxy-2'-methyl-2'-fluoro-pyrimidinenucleoside phosphonates II, according to the present invention.

Scheme 8 is a non-limiting illustrative example of the synthesis of 5'-deoxy-2'-fluoronucleoside phosphonates I and III (n=1), according to the present invention.

Scheme 9 is a non-limiting illustrative example of the synthesis of 5'-methylene-2'-fluoronucleoside phosphonates I and III (n=2), according to the present invention.

DETAILED DESCRIPTION OF THE INVENTION

The invention as disclosed herein is method and composition for the treatment of HIV, hepatitis B or C, or abnormal cellular proliferation, in humans or other host animals, that includes administering an effective amount of a β-D- or β-L-2'-fluoronucleoside phosphonate, a pharmaceutically acceptable derivative, including a compound which has been alkylated or acylated on sugar or phosphonate moiety, or on the purine or pyrimidine, or a pharmaceutically acceptable salt thereof, optionally in a pharmaceutically acceptable carrier. The compounds of this invention either possess antiviral (i.e., anti-HIV-1, anti-HIV-2, anti-hepatitis B/C virus) activity or antiproliferative activity, or are metabolized to a compound that exhibits such activity. The invention as disclosed herein also includes the process for the preparation of such β-D- or β-L-2'-fluoronucleoside phosphonates.

In summary, the present invention includes the following features:

(a) β-L and β-D-2'-fluoronucleoside phosphonates (I)-(IV), as described herein, and pharmaceutically acceptable derivatives and salts thereof;

(b) synthesis of the β-L and β-D-2'-fluoronucleoside phosphonates (I)-(IV), as described herein, and pharmaceutically acceptable derivatives and salts thereof;

(c) β-L and β-D-2'-fluoronucleoside phosphonates (I)-(IV) as described herein, and pharmaceutically acceptable derivatives and salts thereof for use in medical therapy, for example for the treatment or prophylaxis of an HIV, hepatitis B (or C) virus infection or for the treatment of abnormal cellular proliferation;

(d) pharmaceutical formulations comprising the β-D or β-L-2'-fluoronucleoside phosphonates (I)-(IV), or its pharmaceutically acceptable derivative or salt thereof, together with a pharmaceutically acceptable carrier or diluent;

(e) pharmaceutical formulations comprising the β-D or β-L-2'-fluoronucleoside phosphonates (I)-(IV), or its pharmaceutically acceptable derivative or salt thereof, together with another active ingredient, such as another antiviral agent or antiproliferative agent;

(f) methods to treat a host suffering from an HIV infection, hepatitis B virus infection or abnormal cellular proliferation, comprising administering an effective amount of a β-D or β-L-2'-fluoronucleoside phosphonate (I)-(IV), or its pharmaceutically acceptable derivative or salt thereof;

(g) methods to treat a host suffering from an HIV infection, hepatitis B virus infection or abnormal cellular proliferation, comprising administering an effective amount of a β-D or β-L-2'-fluoronucleoside phosphonate (I)-(IV), or its pharmaceutically acceptable derivative or salt thereof, in combination or alternation with another active ingredient, such as another antiviral agent or antiproliferative agent;

(h) use of a β-D or β-L-2'-fluoronucleoside phosphonate (I)-(IV), or its pharmaceutically acceptable derivative or salt thereof, in medical therapy, for example for the treatment or prophylaxis of an HIV infection, an hepatitis B virus infection or an abnormal cellular proliferation;

(f) use of a β-D or β-L-2'-fluoronucleoside phosphonate (I)-(IV), or its pharmaceutically acceptable derivative or salt thereof, as an antiviral;

(g) use of a β-D or β-L-2'-fluoronucleoside phosphonate (I)-(IV), or its pharmaceutically acceptable derivative or salt thereof, as an antiproliferative;

(h) use of a β-D or β-L-2'-fluoronucleoside phosphonate (I)-(IV), or it pharmaceutically acceptable derivative or salt thereof, in combination or alternation with another active ingredient, such as another antiviral agent or antiproliferative agent in medical therapy, for example for the treatment or prophylaxis of an HIV infection, an hepatitis B virus infection or abnormal cellular proliferation;

(i) use of a β-D or β-L-2'-fluoronucleoside phosphonate (I)-(IV), or it pharmaceutically acceptable derivative or salt thereof, for treatment or prophylaxis of an HIV infection, an hepatitis B virus infection or abnormal cellular proliferation;
(j) use of a β-D or β-L-2'-fluoronucleoside phosphonate (I)-(IV), or it pharmaceutically acceptable derivative or salt thereof, in the manufacture of a medicament for treatment or prophylaxis of an HIV infection, an hepatitis B virus infection or abnormal cellular proliferation; and
(k) processes for the preparation of β-L and β-D-2'-halo-4'-thionucleosides, as described in more detail below.

I. Active Compound

In one embodiment, the compound of the invention is a 2'-fluoronucleoside phosphonate of the general formula (I)-(IV):

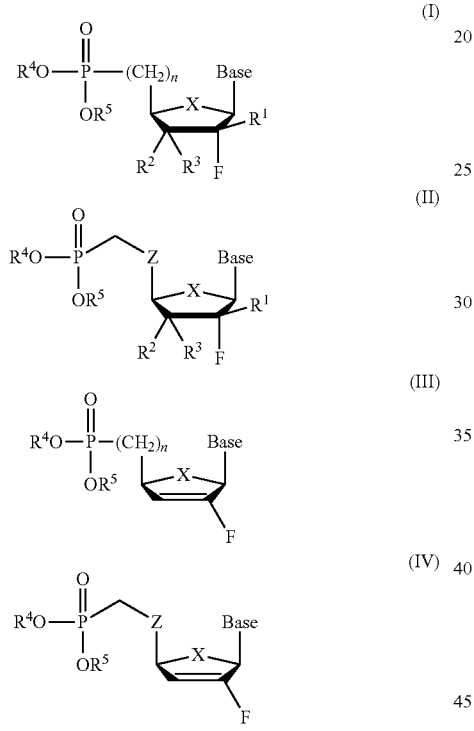

or its pharmaceutically acceptable salt or prodrug thereof, wherein:
(i) X is O, S, $SO_2$, or $CH_2$;
(j) Z is O, S, or NH;
(k) n is 1 or 2;
(l) $R^1$ is H or $CH_3$;
(m) $R^2$ and $R^3$ are independently a hydrogen, halogen (F, Cl, Br, I), OH, OR', SH, SR', $N_3$, $NH_2$, NHR', CN, OCOR', OCOOR', lower alkyl of $C_1$-$C_6$, halogenated (F, Cl, Br, I) lower alkyl of $C_1$-$C_6$ such as $CF_3$ and $CH_2CH_2F$, lower alkenyl of $C_2$-$C_6$ such as $CH=CH_2$, halogenated (F, Cl, Br, I) lower alkenyl of $C_2$-$C_6$ such as $CH=CHCl$, $CH=CHBr$ and $CH=CHI$, lower alkynyl of $C_2$-$C_6$ such as $C≡CH$, halogenated (F, Cl, Br, I) lower alkynyl of $C_2$-$C_6$, lower alkoxy of $C_1$-$C_6$ such as $CH_2OH$ and $CH_2CH_2OH$, lower alkyl acid of $C_2$-$C_6$ such as $CH_2COOH$ and $CH_2CH_2COOH$, lower alkyl acid ester of $C_2$-$C_6$ such as $CH_2COOR'$ and $CH_2CH_2COOR'$;
(n) $R^4$ and $R^5$ are independently a hydrogen, phosphate, diphosphate, or a group that is preferentially removed in a hepatocyte to yield the corresponding OH group. The term "preferentially removed in a hepatocyte" as used herein means at least part of the group is removed in a hepatocyte at a rate higher than the rate of removal of the same group in a non-hepatocytic cell (e.g., fibroblast or lymphocyte). It is therefore contemplated that the removable group includes all pharmaceutically acceptable groups that can be removed by a reductase, esterase, cytochrome P450 or any other specific liver enzyme. Alternative contemplated groups may also include groups that are not necessarily preferentially removed in a hepatocyte, but effect at least some accumulation and/or specific delivery to a hepatocyte (e.g., esters with selected amino acids, including valine, leucine, isoleucine, or polyarginine or polyaspartate);
(o) Base is a heterocycle containing at least one nitrogen, preferably pyrimidine or purine base of the general formula of (V)-(VI):

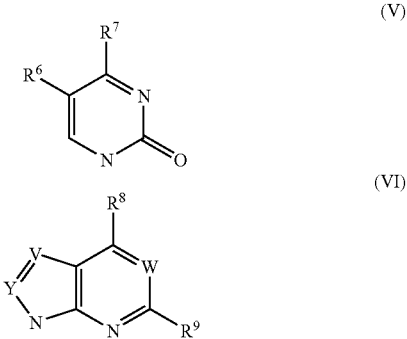

or its pharmaceutically acceptable salt or prodrug thereof, wherein:
(v) W, Y and V are independently N, CH, or $CR^{10}$;
(vi) $R^6$ is a hydrogen, halogen (F, Cl, Br, I), OH, OR', SH, SR', $NH_2$, NHR', $NR'_2$, COOH, COOR', $CONH_2$, CONHR', $CONR'_2$, $CH=CHCO_2H$, $CH=CHCO_2R'$, lower alkyl of $C_1$-$C_6$, halogenated (F, Cl, Br, I) lower alkyl of $C_1$-$C_6$ such as $CF_3$ and $CH_2CH_2F$, lower alkenyl of $C_2$-$C_6$ such as $CH=CH_2$, halogenated (F, Cl, Br, I) lower alkenyl of $C_2$-$C_6$ such as $CH=CHCl$, $CH=CHBr$ and $CH=CHI$, lower alkynyl of $C_2$-$C_6$ such as $C≡CH$, halogenated (F, Cl, Br, I) lower alkynyl of $C_2$-$C_6$, lower alkoxy of $C_1$-$C_6$ such as $CH_2OH$ and $CH_2CH_2OH$, lower alkyl acid of $C_2$-$C_6$ such as $CH_2COOH$ and $CH_2CH_2COOH$, lower alkyl acid ester of $C_2$-$C_6$ such as $CH_2COOR'$ and $CH_2CH_2COOR'$;
(vii) $R^7$, $R^8$ and $R^9$ are independently a hydrogen, halogen (F, Cl, Br, I), OH, OR', SH, SR', $NH_2$, NHR', $NR'_2$, OCOR', OCOOR', NHCOR', NHCOOR';
(viii) $R^{10}$ is a halogen, alkyl, ary, acyl;
(p) each R' is independently a hydrogen, lower alkyl of $C_1$-$C_6$ or lower cycloalkyl of $C_1$-$C_6$;

In a particular embodiment of the present invention, a β-D 2'-fluoronucleoside phosphonate of the formula:

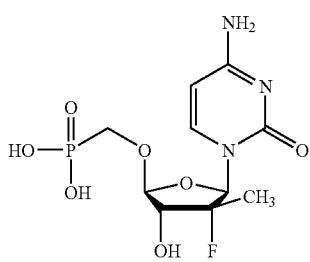

its β-L enantiomer, or its pharmaceutically acceptable salt or prodrug thereof, is provided for the treatment or prophylaxis of a viral infection, including HIV, HBV, and HCV, or a disease associated with abnormal cellular proliferation, and in particular a malignant tumor.

In another particular embodiment of the present invention, a β-D 2'-fluoronucleoside phosphonate of the formula:

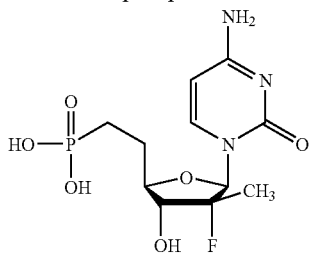

its β-L enantiomer, or its pharmaceutically acceptable salt or prodrug thereof, is provided for the treatment or prophylaxis of a viral infection, including HIV, HBV, and HCV, or a disease associated with abnormal cellular proliferation, and in particular a malignant tumor.

In yet another particular embodiment of the present invention, a β-D 2'-fluoronucleoside phosphonate of the formula:

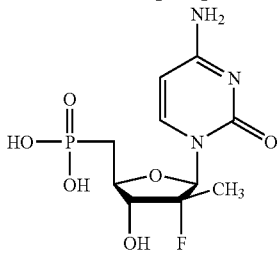

its β-L enantiomer, or its pharmaceutically acceptable salt or prodrug thereof, is provided for the treatment or prophylaxis of a viral infection, including HIV, HBV, and HCV, or a disease associated with abnormal cellular proliferation, and in particular a malignant tumor.

In yet another particular embodiment of the present invention, a β-D 2'-fluoronucleoside phosphonate of the formula:

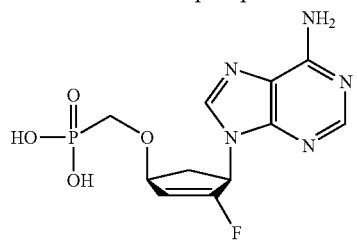

its β-L enantiomer, or its pharmaceutically acceptable salt or prodrug thereof, is provided for the treatment or prophylaxis of a viral infection, including HIV, HBV, and HCV, or a disease associated with abnormal cellular proliferation, and in particular a malignant tumor.

In yet another particular embodiment of the present invention, a β-D 2'-fluoronucleoside phosphonate of the formula:

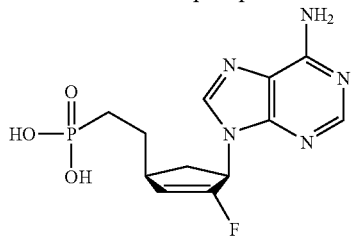

its β-L enantiomer, or its pharmaceutically acceptable salt or prodrug thereof, is provided for the treatment or prophylaxis of a viral infection, including HIV, HBV, and HCV, or a disease associated with abnormal cellular proliferation, and in particular a malignant tumor.

In yet another particular embodiment of the present invention, a β-D 2'-fluoronucleoside phosphonate of the formula:

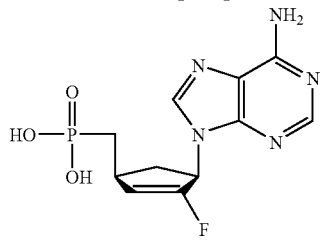

its β-L enantiomer, or its pharmaceutically acceptable salt or prodrug thereof, is provided for the treatment or prophylaxis of a viral infection, including HIV, HBV, and HCV, or a disease associated with abnormal cellular proliferation, and in particular a malignant tumor.

In yet another particular embodiment of the present invention, a β-D 2'-fluoronucleoside phosphonate of the formula:

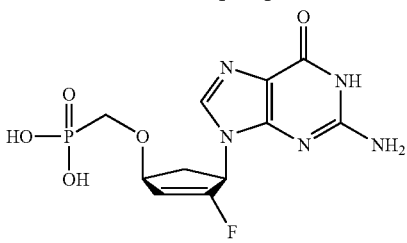

its β-L enantiomer, or its pharmaceutically acceptable salt or prodrug thereof, is provided for the treatment or prophylaxis of a viral infection, including HIV, HBV, and HCV, or a disease associated with abnormal cellular proliferation, and in particular a malignant tumor.

In yet another particular embodiment of the present invention, a β-D 2'-fluoronucleoside phosphonate of the formula:

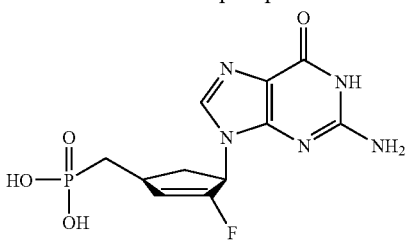

its β-L enantiomer, or its pharmaceutically acceptable salt or prodrug thereof, is provided for the treatment or prophylaxis of a viral infection, including HIV, HBV, and HCV, or a disease associated with abnormal cellular proliferation, and in particular a malignant tumor.

In yet another particular embodiment of the present invention, a β-D 2'-fluoronucleoside phosphonate of the formula:

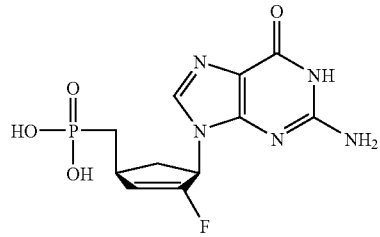 [SMILES: Nc1nc2c(ncn2[C@@H]2C[C@H](CP(=O)(O)O)C=C2F)c(=O)[nH]1]

its β-L enantiomer, or its pharmaceutically acceptable salt or prodrug thereof, is provided for the treatment or prophylaxis of a viral infection, including HIV, HBV, and HCV, or a disease associated with abnormal cellular proliferation, and in particular a malignant tumor.

In one embodiment of the invention, the 2'-fluoronucleoside phosphonate of the invention is the isolated β-D or β-L isomer. In another embodiment of the invention, the 2'-fluoronucleoside phosphonates are enantiomerically enriched. In yet another embodiment of the invention, the 2'-fluoronucleoside phosphonate is in a enantiomeric mixture in which the desired enantiomer is at least 95%, 98% or 99% free of its enantiomer.

In another embodiment, the 2'-fluoronucleoside phosphonate has an $EC_{50}$ (effective concentration to achieve 50% inhibition) when tested in an appropriate cell-based assay, of less than 15 micromolar, and more particularly, less than 10 or 5 micromolar. In a preferred embodiment, the nucleoside is enantiomerically enriched.

In one embodiment of the present invention, the compounds of the formula (I)-(IV) are in the β-D configuration. In an alternate embodiment of the present invention, the compounds of formula (I)-(IV) are in the β-L configuration.

The 2'-fluoronucleoside phosphonates depicted above are in the β-D configuration, however, it should be understood that the 2'-fluoronucleoside phosphonates can be either in the β-L or β-D configuration.

II. Stereoisomerism and Polymorphism

The compounds of the present invention may have asymmetric centers and occur as racemates, racemic mixtures, individual diastereomers or enantiomers, with all isomeric forms being included in the present invention. Compounds of the present invention having a chiral center may exist in and be isolated in optically active and racemic forms. Some compounds may exhibit polymorphism. The present invention encompasses racemic, optically-active, polymorphic, or stereoisomeric form, or mixtures thereof, of a compound of the invention, which possess the useful properties described herein. The optically active forms can be prepared by, for example, resolution of the racemic form by recrystallization techniques, by synthesis from optically-active starting materials, by chiral synthesis, or by chromatographic separation using a chiral stationary phase or by enzymatic resolution.

Optically active forms of the compounds can be prepared using any method known in the art, including but not limited to by resolution of the racemic form by recrystallization techniques, by synthesis from optically-active starting materials, by chiral synthesis, or by chromatographic separation using a chiral stationary phase.

Examples of methods to obtain optically active materials include at least the following.

i) physical separation of crystals: a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization: a technique whereby the individual enantiomers are separately crystallized from a solution of the racemate, possible only if the latter is a conglomerate in the solid state;

iii) enzymatic resolutions: a technique whereby partial or complete separation of a racemate by virtue of differing rates of reaction for the enantiomers with an enzyme;

iv) enzymatic asymmetric synthesis: a synthetic technique whereby at least one step of the synthesis uses an enzymatic reaction to obtain an enantiomerically pure or enriched synthetic precursor of the desired enantiomer;

v) chemical asymmetric synthesis: a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations: a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations: a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions: this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors: a synthetic technique whereby the desired enantiomer is obtained from non-chiral starting materials and where the stereochemical integrity is not or is only minimally compromised over the course of the synthesis;

x) chiral liquid chromatography: a technique whereby the enantiomers of a racemate are separated in a liquid mobile phase by virtue of their differing interactions with a stationary phase (including but not limited to via chiral HPLC). The stationary phase can be made of chiral material or the mobile phase can contain an additional chiral material to provoke the differing interactions;

xi) chiral gas chromatography: a technique whereby the racemate is volatilized and enantiomers are separated by virtue of their differing interactions in the gaseous mobile phase with a column containing a fixed non-racemic chiral adsorbent phase;

xii) extraction with chiral solvents: a technique whereby the enantiomers are separated by virtue of preferential dissolution of one enantiomer into a particular chiral solvent;

xiii) transport across chiral membranes: a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

Chiral chromatography, including but not limited to simulated moving bed chromatography, is used in one embodiment. A wide variety of chiral stationary phases are commercially available.

III. Definitions

The term alkyl, as used herein, unless otherwise specified, refers to a saturated straight, branched, or cyclic, primary, secondary, or tertiary hydrocarbon of $C_1$ to $C_{10}$, and specifically includes methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The alkyl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term lower alkyl, as used herein, and unless otherwise specified, refers to a $C_1$ to $C_4$ saturated straight, branched, or if appropriate, a cyclic (for example, cyclopropyl)alkyl group.

The term alkylamino or arylamino refers to an amino group that has one or two alkyl or aryl substituents, respectively.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis. The term aryl, as used herein, and unless otherwise specified, refers to phenyl, biphenyl, or naphthyl, and preferably phenyl. The aryl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The term alkaryl or alkylaryl refers to an alkyl group with an aryl substituent. The term aralkyl or arylalkyl refers to an aryl group with an alkyl substituent.

The term halo, as used herein, includes chloro, bromo, iodo, and fluoro.

The term purine or pyrimidine base includes, but is not limited to, adenine, $N^6$-alkylpurines, $N^6$-acylpurines (wherein acyl is C(O)(alkyl, aryl, alkylaryl, or arylalkyl)), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrimidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, 2-chloro-2-aminopurine, inosine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, acyl groups such as acetyl and propionyl, methanesulfonyl, and p-toluenesulfonyl.

The term acyl refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group. Acyl can also include a natural or synthetic amino acid moiety.

As used herein, the term "substantially free of" or "substantially in the absence of" refers to a nucleoside composition that includes at least 95% to 98%, or more preferably, 99% to 100%, of the designated enantiomer of that nucleoside.

Similarly, the term "isolated" refers to a nucleoside composition that includes at least 85 or 90% by weight, preferably 95% to 98% by weight, and even more preferably 99% to 100% by weight, of the nucleoside, the remainder comprising other chemical species or enantiomers.

The term host, as used herein, refers to a unicellular or multicellular organism in which the virus can replicate, including cell lines and animals, and preferably a human, or a unicellular or multicellular organism in which the conditions of abnormal cellular proliferation can be mimicked. For example, in the case of HIV, HBV or HCV, the host is any unicellular or multicellular organism that can be carrying a part of the viral genome, whose replication or function can be altered by the compounds of the present invention. The term host specifically refers to infected cells, cells transfected with all or part of the viral genome and animals, in particular, primates (including chimpanzees) and humans. In most animal applications of the present invention, the host is a human patient. Veterinary applications, in certain indications, however, are clearly anticipated by the present invention (such as chimpanzees).

The term "pharmaceutically acceptable salt or prodrug" is used throughout the specification to describe any pharmaceutically acceptable form (such as an ester, phosphate ester, salt of an ester, acylation or alkylation product or a related derivative) of a nucleoside compound which, upon administration to a patient, provides the nucleoside compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. The compounds of this invention possess antiviral activity against flavivirus or pestivirus, or are metabolized to a compound that exhibits such activity.

IV. Pharmaceutically Acceptable Derivatives

The active compound can be administered as any derivative that upon administration to the recipient, is capable of providing directly or indirectly, the parent compound. Further, the modifications can affect the biological activity of the compound, in some cases increasing the activity over the parent compound. This can easily be assessed by preparing the derivative and testing its antiviral activity according to the methods described herein, or other method known to those skilled in the art.

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, ⟨-ketoglutarate, and ⟨-glycerophosphate. Suitable inorganic salts may also be formed, including, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Any of the nucleosides described herein can be administrated as a nucleotide prodrug to increase the activity, bioavailability, stability or otherwise alter the properties of the nucleoside. A number of nucleotide prodrug ligands are known. In general, alkylation, acylation or other lipophilic modification of the mono, di or triphosphate of the nucleoside will increase the stability of the nucleotide. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischofberger, *Antiviral Research*, 27 (1995) 1-17. Any of these can be used in combination with the disclosed nucleosides to achieve a desired effect.

The active nucleoside can also be provided as a 5'-phosphoether lipid or a 5'-ether lipid, as disclosed in the following references, which are incorporated by reference herein: Kucera, L. S., N. Iyer, E. Leake, A. Raben, Modest E. K., D. L. W., and C. Piantadosi. 1990. "Novel membrane-interactive ether lipid analogs that inhibit infectious HIV-1 production and induce defective virus formation." *AIDS Res. Hum. Retro Viruses*. 6:491-501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest. 1991. "Synthesis and evaluation of novel ether lipid nucleoside conjugates for anti-HIV activity." *J. Med. Chem.* 34:1408.1414; Hosteller, K. Y., D. D. Richman, D. A. Carson, L. M. Stuhmiller, G. M. T. van Wijk, and H. van den Bosch. 1992. "Greatly enhanced inhibition of human immunodeficiency virus type 1 replication in CEM and HT4-6C cells by 3'-deoxythymidine diphosphate dimyristoylglycerol, a lipid prodrug of 3,-deoxythymidine." *Antimicrob. Agents Chemother.* 36:2025.2029; Hosetler, K. Y., L. M. Stuhmiller, H. B. Lenting, H. van den Bosch, and D. D. Richman, 1990. "Synthesis and antiretroviral activity of phospholipid analogs of azidothymidine and other antiviral nucleosides." *J. Biol. Chem.* 265:61127.

Nonlimiting examples of U.S. patents that disclose suitable lipophilic substituents that can be covalently incorporated into the nucleoside, preferably at the 5'-OH position of the nucleoside or lipophilic preparations, include U.S. Pat. No. 5,149,794 (Sep. 22, 1992, Yatvin et al.); U.S. Pat. No. 5,194,654 (Mar. 16, 1993, Hostetler et al., U.S. Pat. No. 5,223,263 (Jun. 29, 1993, Hostetler et al.); U.S. Pat. No. 5,256,641 (Oct. 26, 1993, Yatvin et al.); U.S. Pat. No. 5,411,947 (May 2, 1995, Hostetler et al.); U.S. Pat. No. 5,463,092 (Oct. 31, 1995, Hostetler et al.); U.S. Pat. No. 5,543,389 (Aug. 6, 1996, Yatvin et al.); U.S. Pat. No. 5,543,390 (Aug. 6, 1996, Yatvin et al.); U.S. Pat. No. 5,543,391 (Aug. 6, 1996, Yatvin et al.); and U.S. Pat. No. 5,554,728 (Sep. 10, 1996; Basava et al.), all of which are incorporated herein by reference. Foreign patent publications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

Nonlimiting examples of nucleotide prodrugs are described in the following references: Ho, D. H. W. (1973) "Distribution of Kinase and deaminase of 1β-D-arabinofuranosylcytosine in tissues of man and muse." *Cancer Res.* 33, 2816-2820; Holy, A. (1993) Isopolar phosphorous-modified nucleotide analogues," In: De Clercq (Ed.), *Advances in Antiviral Drug Design*, Vol. I, JAI Press, pp. 179-231; Hong, C. I., Nechaev, A., and West, C. R. (1979a) "Synthesis and antitumor activity of 1-β-D-arabino-furanosylcytosine conjugates of cortisol and cortisone." *Bicohem. Biophys. Rs. Commun.* 88, 1223-1229; Hong, C. I., Nechaev, A., Kirisits, A. J. Buchheit, D. J. and West, C. R. (1980) "Nucleoside conjugates as potential antitumor agents. 3. Synthesis and antitumor activity of 1-(β-D-arabinofuranosyl)cytosine conjugates of corticosteriods and selected lipophilic alcohols." *J. Med. Chem.* 28, 171-177; Hostetler, K. Y., Stuhmiller, L. M., Lenting, H. B. M. van den Bosch, H. and Richman *J. Biol. Chem.* 265, 6112-6117; Hostetler, K. Y., Carson, D. A. and Richman, D. D. (1991); "Phosphatidylazidothymidine: mechanism of antiretroviral action in CEM cells." *J. Biol. Chem.* 266, 11714-11717; Hostetler, K. Y., Korba, B. Sridhar, C., Gardener, M. (1994a) "Antiviral activity of phosphatidyldideoxycytidine in hepatitis B-infected cells and enhanced hepatic uptake in mice." *Antiviral Res.* 24, 59-67; Hosteller, K. Y., Richman, D. D., Sridhar. C. N. Felgner, P. L. Felgner, J., Ricci, J., Gardener, M. F. Selleseth, D. W. and Ellis, M. N. (1994b) "Phosphatidylazidothymidine and phosphatidylddC: Assessment of uptake in mouse lymphoid tissues and antiviral activities in human immunodeficiency virus-infected cells and in rauscher leukemia virus-infected mice." *Antimicrobial Agents Chemother.* 38, 2792-2797; Hunston, R. N., Jones, A. A. McGuigan, C., Walker, R. T., Balzarini, J., and DeClercq, E. (1984) "Synthesis and biological properties of some cyclic phosphotriesters derived from 2'-deoxy-5-fluorouridine." *J. Med. Chem.* 27, 440-444; Ji, Y. H., Moog, C., Schmitt, G., Bischoff, P. and Luu, B. (1990); "Monophosphoric acid esters of 7-®-hydroxycholesterol and of pyrimidine nucleoside as potential antitumor agents: synthesis and preliminary evaluation of antitumor activity." *J. Med. Chem.* 33 2264-2270; Jones, A. S., McGuigan, C., Walker, R. T., Balzarini, J. and DeClercq, E. (1984) "Synthesis, properties, and biological activity of some nucleoside cyclic phosphoramidates." *J. Chem. Soc. Perkin Trans. I,* 1471-1474; Juodka, B. A. and Smrt, J. (1974) "Synthesis of diribonucleoside phosph (P→N) amino acid derivatives." *Coll. Czech. Chem. Comm.* 39, 363-968; Kataoka, S., Imai, J., Yamaji, N., Kato, M., Saito, M., Kawada, T. and Imai, S. (1989) "Alkylated cAMP derivatives; selective synthesis and biological activities." *Nucleic Acids Res. Sym. Ser.* 21, 1-2; Kataoka, S., Uchida, "(cAMP) benzyl and methyl triesters." *Heterocycles* 32, 1351-1356; Kinchington, D., Harvey, J. J., O'Connor, T. J., Jones, B. C. N. M., Devine, K. G., Taylor-Robinson D., Jeffries, D. J. and McGuigan, C. (1992) "Comparison of antiviral effects of zidovudine phosphoramidate and phosphorodiamidate derivates against HIV and ULV in vitro." *Antiviral Chem. Chemother.* 3, 107-112; Kodama, K., Morozumi, M., Saithoh, K. I., Kuninaka, H., Yosino, H. and Saneyoshi, M. (1989) "Antitumor activity and pharmacology of 1-β-D-arabinofuranosylcytosine-5'-stearylphosphate; an orally active derivative of 1-β-D-arabinofuranosylcytosine." *Jpn. J. Cancer Res.* 80, 679-685; Korty, M. and Engels, J. (1979) "The effects of adenosine- and guanosine 3',5' phosphoric and acid benzyl esters on guinea-pig ventricular myocardium." *Naunyn-Schmiedeberg's Arch. Pharmacol.* 310, 103-111; Kumar, A., Goe, P. L., Jones, A. S. Walker, R. T. Balzarini, J. and DeClercq, E. (1990) "Synthesis and biological evaluation of some cyclic phosphoramidate nucleoside derivatives." *J. Med. Chem.,* 33, 2368-2375; LeBec, C., and Huynh-Dinh, T. (1991) "Synthesis of lipophilic phosphate triester derivatives of 5-fluorouridine an arabinocytidine as anticancer prodrugs." *Tetrahedron Lett.* 32, 6553-6556; Lichtenstein, J., Barner, H. D. and Cohen, S. S. (1960) "The metabolism of exogenously supplied nucleotides by *Escherichia coli.,*" *J. Biol. Chem.* 235, 457-465; Luethy, J., Von Daeniken, A., Friederich, J. Manthey, B., Zweifel, J., Schlatter, C. and Benn, M. H. (1981) "Synthesis and toxicological properties of three naturally occurring cyanoepithioalkanes". *Mitt. Geg. Lebensmittelunters. Hyg.* 72, 131-133 (*Chem. Abstr.* 95, 127093); McGigan, C. Tollerfield, S. M. and Riley, P. a. (1989) "Synthesis and biological evaluation of some phosphate triester derivatives of the anti-viral drug Ara." *Nucleic Acids Res.* 17, 6065-6075; McGuigan, C., Devine, K. G., O'Connor, T. J., Galpin, S. A., Jeffries, D. J. and Kinchington, D. (1990a) "Synthesis and evaluation of some novel phosphoramidate derivatives of 3'-azido-3'-deoxythymidine (AZT) as anti-HIV compounds." Antiviral Chem. Chemother. 1 107-113; McGuigan, C., O'Connor, T. J., Nicholls, S. R. Nickson, C. and Kinchington, D. (1990b) "Synthesis and anti-HIV activity of some novel substituted dialkyl phosphate derivatives of AZT and ddCyd." *Antiviral Chem. Chemother.* 1, 355-360; McGuigan, C., Nicholls, S. R., O'Connor, T. J., and Kinchington, D. (1990c) "Synthesis of some novel dialkyl phosphate derivative of 3'-modified nucleosides as potential anti-AIDS drugs." *Antiviral Chem. Chemother.* 1, 25-33; McGuigan, C., Devin, K. G., O'Connor, T. J., and Kinchington, D. (1991) "Synthesis and anti-HIV activity of some haloalkyl phosphoramidate derivatives of 3'-azido-3'-deoxythylmidine (AZT); potent activity of the trichloroethyl methoxyalaninyl compound." *Antiviral Res.* 15, 255-263; McGuigan, C., Pathirana, R. N., Balzarini, J. and DeClercq, E. (1993b) "Intracellular delivery of bioactive AZT nucleotides by aryl phosphate derivatives of AZT." *J. Med. Chem.* 36, 1048-1052; Wagner, C. R., Iyer, V. V., McIntee, E. J. (2000) "Pronucleotides: towards the in vivo delivery of antiviral and anticancer nucleotides." *Med. Res. Rev.* 20, 417-451; Meier, C. (2002) "cycloSal-pronucleotides-design of chemical Trojan horses." *Mini Rev. Med. Chem.* 2, 219-234; Cahard, D., McGuigan, C. Balzarini, J. (2004a) "Aryloxy phosphoramidate trimesters as pro-tides." *Mini Rev. Med. Chem.* 4, 371-381; Peyrottes, S., Egron, D., Lefebvre, I., Gosselin, G., Imbach, J.-L., Perigaud, C. (2004b) "SATE pronucleotide approaches: an overview." *Mini Rev. Med. Chem.* 4, 395-408; Drontle, D. P., Wagner, C. R. (2004c) "Design a pronucleotide stratagem: lessons from amino acid phosphoramidates of anticancer and antiviral pyrimidines." *Mini Rev. Med. Chem.* 4, 409-419.

Alkyl hydrogen phosphate derivatives of the anti-HIV agent AZT may be less toxic than the parent nucleoside analogue. *Antiviral Chem. Chemother.* 5, 271-277; Meyer, R. B., Jr., Shuman, D. A. and Robins, R. K. (1973) "Synthesis of purine nucleoside 3',5'-cyclic phosphoramidates." *Tetrahedron Lett.* 269-272; Nagyvary, J. Gohil, R. N., Kirchner, C. R. and Stevens, J. D. (1973) "Studies on neutral esters of cyclic AMP," *Biochem. Biophys. Res. Commun.* 55, 1072-1077; Namane, A. Gouyette, C., Fillion, M. P., Fillion, G. and Huynh-Dinh, T. (1992) "Improved brain delivery of AZT using a glycosyl phosphotriester prodrug." *J. Med. Chem.* 35, 3039-3044; Nargeot, J. Nerbonne, J. M. Engels, J. and Leser, H. A. (1983) *Natl. Acad. Sci. USA.* 80, 2395-2399; Nelson, K. A., Bentrude, W. G. Stser, W. N. and Hutchinson, J. P. (1987) "The question of chair-twist equilibria for the phosphate rings of nucleoside cyclic 3', 5' monophosphates. $^1$HNMR and x-ray crystallographic study of the diastereomers of thymidine phenyl cyclic 3',5'-monophosphate." *J. Am. Chem. Soc.* 109, 4058-4064; Nerbonne, J. M., Richard, S., Nargeot, J. and Lester, H. A. (1984) "New photoactivatable cyclic nucleotides produce intracellular jumps in cyclic AMP and cyclic GMP concentrations." *Nature* 301, 74-76; Neumann, J. M., Herv_, M., Debouzy, J. C., Guerra, F. I., Gouyette, C., Dupraz, B. and Huyny-Dinh, T. (1989) "Synthesis and transmembrane transport studies by NMR of a glucosyl phospholipid of thymidine." *J. Am. Chem. Soc.* 111, 4270-4277; Ohno, R., Tatsumi, N., Hirano, M., Imai, K. Mizoguchi, H., Nakamura, T., Kosaka, M., Takatuski, K., Yamaya, T., Toyama K., Yoshida, T., Masaoka, T., Hashimoto, S., Ohshima, T., Kimura, I., Yamada, K. and Kimura, J. (1991) "Treatment of myelodysplastic syndromes with orally administered 1-β-D-arabinouranosylcytosine-5' stearylphosphate." *Oncology* 48, 451-455. Palomino, E., Kessle, D. and Horwitz, J. P. (1989) "A dihydropyridine carrier system for sustained delivery of 2', 3' dideoxynucleosides to the brain." *J. Med. Chem.* 32, 22-625; Perkins, R. M., Barney, S. Wittrock, R., Clark, P. H., Levin, R. Lambert, D. M., Petteway, S. R., Serafinowska, H. T., Bailey, S. M., Jackson, S., Harnden, M. R. Ashton, R., Sutton, D., Harvey, J. J. and Brown, A. G. (1993) "Activity of BRL47923 and its oral prodrug, SB203657A against a rauscher murine leukemia virus infection in mice." *Antiviral Res.* 20 (Suppl. I). 84; Piantadosi, C., Marasco, C. J., Jr., Norris-Natschke, S. L., Meyer, K. L., Gumus, F., Surles, J. R., Ishaq, K. S., Kucera, L. S. Iyer, N., Wallen, C. A., Piantadosi, S, and Modest, E. J. (1991) "Synthesis and evaluation of novel ether lipid nucleoside conjugates for anti-HIV-1 activity." *J. Med. Chem.* 34, 1408-1414; Pompon, A., Lefebvre, I., Imbach, J. L., Kahn, S, and Farquhar, D. (1994). "Decomposition pathways of the mono- and bis(pivaloyloxymethyl)esters of azidothymidine-5'-monophosphate in cell extract and in tissue culture medium; an application of the 'on-line ISRP-cleaning HPLC technique." *Antiviral Chem. Chemother.* 5, 91-98; Postemark, T. (1974) "Cyclic AMP and cyclic GMP." *Annu. Rev. Pharmacol.* 14, 23-33; Prisbe, E. J., Martin, J. C. M., McGhee, D. P. C., Barker, M. F., Smee, D. F. Duke, A. E., Matthews, T. R. and Verheyden, J. P. J. (1986) "Synthesis and antiherpes virus activity of phosphate an phosphonate derivatives of 9-[(1,3-dihydroxy-2-propoxy)methyl]guanine." *J. Med. Chem.* 29, 671-675; Pucch, F., Gosselin, G., Lefebvre, I., Pompon, a., Aubertin, A. M. Dirn, and Imbach, J. L. (1993) "Intracellular delivery of nucleoside monophosphate through a reductase-mediated activation process." *Antiviral Res.* 22, 155-174; Pugaeva, V. P., Klochkeva, S. I., Mashbits, F. D. and Eizengart, R. S. (1969). "Toxicological assessment and health standard ratings for ethylene sulfide in the industrial atmosphere." *Gig Trf. Prof Zabol.* 14, 47-48 (*Chem. Abstr.* 72, 212); Robins, R. K. (1984) "The potential of nucleotide analogs as inhibitors of Retro viruses and tumors." *Pharm. Res.* 11-18; Rosowsky, A., Kim. S. H., Ross and J. Wick, M. M. (1982) "Lipophilic 5'-(alkylphosphate) esters of 1-β-D-arabinofuranosylcytosine and its $N^4$-acyl and 2.2'-anhydro-3'-O-acyl derivatives as potential prodrugs." *J. Med. Chem.* 25, 171-178; Ross, W. (1961) "Increased sensitivity of the walker turnout towards aromatic nitrogen mustards carrying basic side chains following glucose pretreatment." *Biochem. Pharm.* 8, 235-240; Ryu, E. K., Ross, R. J. Matsushita, T., MacCoss, M., Hong, C. I. and West, C. R. (1982). "Phospho-lipid-nucleoside conjugates. 3. Synthesis and preliminary biological evaluation of 1-β-D-arabinofuranosylcytosine 5'-diphosphate[-], 2-diacylglycerols." *J. Med. Chem.* 25, 1322-1329; Saffhill, R. and Hume, W. J. (1986) "The degradation of 5-iododeoxyuridine and 5-bromoethoxyuridine by serum from different sources and its consequences for the use of these compounds for incorporation into DNA." *Chem. Biol. Interact.* 57, 347-355; Saneyoshi, M., Morozumi, M., Kodama, K., Machida, J., Kuninaka, A. and Yoshino, H. (1980) "Synthetic nucleosides and nucleotides. XVI. Synthesis and biological evaluations of a series of 1-β-D-arabino-furanosylcytosine 5'-alky or arylphosphates." *Chem. Pharm. Bull.* 28, 2915-2923; Sastry, J. K., Nehete, P. N., Khan, S., Nowak, B. J., Plunkett, W., Arlinghaus, R. B. and Farquhar, D. (1992) "Membrane-permeable dideoxyuridine 5'-monophosphate analogue inhibits human immunodeficiency virus infection." *Mol. Pharmacol.* 41, 441-445; Shaw, J. P., Jones, R. J. Arimilli, M. N., Louie, M. S., Lee, W. A. and Cundy, K. C. (1994) "Oral bioavailability of PMEA from PMEA prodrugs in male Sprague-Dawley rats." *9th Annual AAPS Meeting*. San Diego, Calif. (Abstract). Shuto, S., Ueda, S., Imamura, S., Fukukawa, K. Matsuda, A. and Ueda, T. (1987) "A facile one-step synthesis of 5' phosphatidylnucleosides by an enzymatic two-phase reaction." *Tetrahedron Lett.* 28, 199-202; Shuto, S. Itoh, H., Ueda, S., Imamura, S., Kukukawa, K., Tsujino, M., Matsuda, A. and Ueda, T. (1988) *Pharm. Bull.* 36, 209-217. An example of a useful phosphate prodrug group is the S-acyl-2-thioethyl group, also referred to as "SATE".

V. Combination and Alternation Therapy for HIV, HBV or HCV

It has been recognized that drug-resistant variants of HIV, HBV and HCV can emerge after prolonged treatment with an antiviral agent. Drug resistance most typically occurs by mutation of a gene that encodes for an enzyme used in viral replication, and most typically in the case of HIV, reverse transcriptase, protease, or DNA polymerase, and in the case of HBV, DNA polymerase. Recently, it has been demonstrated that the efficacy of a drug against HIV infection can be prolonged, augmented, or restored by administering the compound in combination or alternation with a second, and perhaps third, antiviral compound that induces a different mutation from that caused by the principle drug. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

The second antiviral agent for the treatment of HIV, in one embodiment, can be a reverse transcriptase inhibitor (a "RTI"), which can be either a synthetic nucleoside (a "NRTI") or a non-nucleoside compound (a "NNRTI"). In an alternative embodiment, in the case of HIV, the second (or third) antiviral agent can be a protease inhibitor. In other embodiments, the second (or third) compound can be a pyrophosphate analog, or a fusion binding inhibitor. A list compiling resistance data collected in vitro and in vivo for a number of antiviral compounds is found in Schinazi, et al, Mutations in retroviral genes associated with drug resistance, *International Antiviral News*, 1997.

Preferred compounds for combination or alternation therapy for the treatment of HBV include 3TC, FTC, L-FMAU, interferon, adefovir dipivoxil, entecavir, telbivudine (L-dT), valtorcitabine (3'-valinyl L-dC), β-D-dioxolanyl-guanine (DXG), β-D-dioxolanyl-2,6-diaminopurine (DAPD), and β-D-dioxolanyl-6-chloropurine (ACP), famciclovir, penciclovir, lobucavir, ganciclovir, and ribavarin.

Preferred examples of antiviral agents that can be used in combination or alternation with the compounds disclosed herein for HIV therapy include cis-2-hydroxymethyl-5-(5-fluorocytosin-1-yl)-1,3-oxathiolane (FTC); the (–)-enantiomer of 2-hydroxymethyl-5-(cytosin-1-yl)-1,3-oxathiolane (3TC); ziagen (abacavir), emtriva, viread (tenofovir DF), carbovir, acyclovir, foscarnet, interferon, AZT, DDI, D4T, CS-87 (3'-azido-2',3'-dideoxyuridine), and β-D-dioxolane nucleosides such as β-D-dioxolanyl-guanine (DXG), β-D-dioxolanyl-2,6-diaminopurine (DAPD), and β-D-dioxolanyl-6-chloropurine (ACP), and integrase inhibitors such as MK-0518.

Preferred protease inhibitors (PIs) include crixivan (indinavir), viracept (nelfinavir), norvir (ritonavir), invirase (saquinavir), aptivus (tipranavir), kaletra, lexiva (fosamprenavir), reyataz (atazanavir) and TMC-114.

Preferred Non-Nucleoside Reverse Transcriptase Inhibitors (NNRTIs) include rescripton (delavirdine), sustiva (efavirenz), viramune (nevirapine) and TMC-125.

Preferred Entry inhibitors include fuzeon (T-20), PRO-542, TNX-355, vicriviroc, aplaviroc and maraviroc.

A more comprehensive list of compounds that can be administered in combination or alternation with any of the disclosed nucleosides include (1S,4R)-4-[2-amino-6-cyclopropyl-amino)-9H-purin-9-yl]-2-cyclopentene-1-methanol succinate ("1592", a carbovir analog; GlaxoWellcome); 3TC: (–)-β-L-2',3'-dideoxy-3'-thiacytidine (GlaxoWellcome); a-APA R18893: a-nitro-anilino-phenylacetamide; A-77003; C2 symmetry-based protease inhibitor (Abbott); A-75925: C2 symmetry-based protease inhibitor (Abbott); AAP-BHAP: bishetero-arylpiperazine analog (Upjohn); ABT-538: C2-symmetry-based protease inhibitor (Abbott); AzddU: 3'-azido-2',3'-dideoxyuridine; AZT: 3'-azido-3'-deoxythymidine (GlaxoWellcome); AZT-p-ddI: 3'-azido-3'-deoxythymidilyl-(5',5')-2',3'-dideoxyinosinic acid (Ivax); BHAP: bishet-eroaryl-piperazine; BILA 1906: N-{1S-[[[3-[2S-{(1,1-dimethylethyl)amino]carbonyl}-4R]-3-pyridinylmethyl) thio]-1-piperidinyl]-2R-hydroxy-1S-(phenylmethyl)-propyl]amino]-carbonyl]-2-methylpropyl}-2-quinolinecarboxamide (Bio Mega/Boehringer-Ingelheim); BILA 2185: N-(1,1-dimethylethyl)-1-[2S-[[2-2,6-dimethyphenoxy)-1-oxoethyl]amino]-2R-hydroxy-4-phenylbutyl]-4R-pyridinylthio)-2-piperidinecarboxamide (BioMega/Boehringer-Ingelheim); BM+51.0836: thiazolo-iso-indolinone derivative; BMS 186,318: aminodiol derivative HIV-1 protease inhibitor (Bristol-Myers-Squibb); d4API: 9-[2,5-dihydro-5-(phosphonomethoxy)-2-furanel]adenine (Gilead); d4C: 2',3'-didehydro-2',3'-dideoxycytidine; d4T: 2',3'-didehydro-3'-deoxythymidine (Bristol-Myers-Squibb); ddC: 2',3'-dideoxycytidine (Roche); ddI: 2',3'-dideoxyinosine (Bristol-Myers-Squibb); DMP-266: a 1,4-dihydro-2H-3,1-benzoxazin-2-one; DMP-450: {[4R-(4-a,5-a,6-b,7-b)]-hexahydro-5,6-bis(hydroxy)-1,3-bis(3-amino)phenyl]-methyl)-4,7-bis-(phenylmethyl)-2H-1,3-diazepin-2-one}-bismesylate (Gilead); DXG: (–)-β-D-dioxolane-guanosine (Gilead); EBU-dM: 5-ethyl-1-ethoxymethyl-6-(3,5-dimethylbenzyl)-uracil; E-EBU: 5-ethyl-1-ethoxymethyl-6-benzyluracil; DS: dextran sulfate; E-EPSeU: 1-(ethoxymethyl)-(6-phenylselenyl)-5-ethyluracil; E-EPU: 1-(ethoxymethyl)-(6-phenyl-thio)-5-ethyluracil; FTC: β-2',3'-dideoxy-5-fluoro-3'-thiacytidine (Gilead); HBY097: S-4-isopropoxycarbonyl-6-methoxy-3-(methylthio-methyl)-3,4-dihydroquinoxalin-2(1H)-thione; HEPT: 1-[(2-hydroxyethoxy)methyl]-6-(phenylthio)thymine; HIV-1: human immunodeficiency virus type 1; JM2763: 1,1'-(1,3-propanediyl)-bis-1,4,8,11-tetraaza-cyclotetradecane (Johnson Matthey); JM3100: 1,1'-[1,4-phenylenebis-(methylene)]-bis-1,4,8,11-tetraazacyclotetradecane (Johnson Matthey); KNI-272: (2S,3S)-3-amino-2-hydroxy-4-phenylbutyric acid-containing tripeptide; L-697,593; 5-ethyl-6-methyl-3-(2-phthalimido-ethyl)pyridin-2(1H)-one; L-735,524: hydroxy-amino-pentane amide HIV-1 protease inhibitor (Merck); L-697,661; 3-{[(-4,7-dichloro-1,3-benzoxazol-2-yl)methyl]amino}-5-ethyl-6-methylpyridin-2(1H)-one; L-FDDC: (–)-β-L-5-fluoro-2',3'-dideoxycytidine; L-FDOC: (–)-β-L-5-fluoro-dioxolane cytosine; MKC442:6-benzyl-1-ethoxymethyl-5-isopropyluracil (1-EBU; Mitsubishi); Nevirapine: 11-cyclo-propyl-5,11-dihydro-4-methyl-6H-dipyridol-[3,2-b:2',3'-e]-diazepin-6-one (Boehringer-Ingelheim); NSC648400: 1-benzyloxymethyl-5-ethyl-6-(alpha-pyridylthio)uracil (E-BPTU); P9941: [2-pyridylacetyl-IlePheAla-y(CHOH)]$_2$ (Dupont Merck); PFA: phosphonoformate (foscarnet; Astra); PMEA: 9-(2-phosphonylmethoxyethyl)adenine (Gilead); PMPA: (R)-9-(2-phosphonylmethoxypropyl)adenine (Gilead); Ro 31-8959: hydroxyethylamine derivative HIV-1 protease inhibitor (Roche); RPI-312: peptidyl protease inhibitor, 1-[(3s)-3-(n-alpha-benzyloxycarbonyl)-1-asparginyl)-amino-2-hydroxy-4-phenylbutyryl]-n-tert-butyl-1-proline amide; 2720: 6-chloro-3,3-dimethyl-4-(isopropenyloxycarbonyl)-3,4-dihydro-quinoxalin-2-(1H)-thione; SC-52151: hydroxy-ethylurea isostere protease inhibitor (Searle); SC-55389A: hydroxyethyl-urea isostere protease inhibitor (Searle); TIBO R82150: (+)-(5S)-4,5,6,7-tetrahydro-5-methyl-6-(3-methyl-2-butenyl)-imidazo[4,5,1-jk][1,4]-benzo-diazepin-2(1H)-thione (Janssen); TIBO 82913: (+)-(5S)-4,5,6,7,-tetrahydro-9-chloro-5-methyl-6-(3-methyl-2-butenyl)imidazo[4,5,1jk]-[1,4]benzo-diazepin-2(1H)-thione (Janssen); TSAO-m3T: [2',5'-bis-O-(tert-butyl-dimethylsilyl)-3'-spiro-5'-(4'-amino-1',2'-oxathiole-2',2'-dioxide)]-β-D-pento-furanosyl-N3-methylthymine; U90152: 1-[3-[(1-methylethyl)-amino]-2-pyridinyl]-4-[[5-[(methylsulphonyl)-amino]-1H-indol-2-yl]carbonyl] piperazine; UC: thiocarboxanilide derivatives (Uniroyal); UC-781: N-[4-chloro-3-(3-methyl-2-butenyloxy)phenyl]-2-methyl-3-furancarbothioamide; UC-82: N-[4-chloro-3-(3-methyl-2-butenyloxy)phenyl]-2-methyl-3-thiophenecarbothioamide; VB 11,328: hydroxyethyl-sulphonamide protease inhibitor (Vertex); VX-478: hydroxyethylsulphonamide protease inhibitor (Vertex); XM 323: cyclic urea protease inhibitor (Dupont Merck).

The active compound can also be administered in combination or alternation with ribavarin, interferon, interleukin or a stabilized prodrug of any of them. More broadly described, the compound can be administered in combination or alternation with any of the anti-HCV drugs listed below.

| Table of anti-Hepatitis C Compounds in Current Clinical Development | | |
|---|---|---|
| Drug Name | Drug Category | Pharmaceutical Company |
| PEGASYS pegylated interferon alfa-2a | Long acting interferon | Roche |
| INFERGEN interferon alfacon-1 | Interferon, Long acting interferon | InterMune |
| OMNIFERON natural interferon | Interferon, Long acting interferon | Viragen |
| ALBUFERON | Longer acting interferon | Human Genome Sciences |
| REBIF interferon beta-1a | Interferon | Ares-Serono |
| Omega Interferon | Interferon | BioMedicine |
| Oral Interferon alpha | Oral Interferon | Amarillo Biosciences |
| Interferon gamma-1b | Anti-fibrotic | InterMune |
| IP-501 | Anti-fibrotic | Interneuron |
| Merimebodib VX-497 | IMPDH inhibitor (inosine monophosphate dehydrogenase) | Vertex |
| AMANTADINE (Symmetrel) | Broad Antiviral Agent | Endo Labs Solvay |
| IDN-6556 | Apotosis regulation | Idun Pharma. |
| XTL-002 | Monclonal Antibody | XTL |
| HCV/MF59 | Vaccine | Chiron |
| CIVACIR | Polyclonal Antibody Therapeutic vaccine | NABI Innogenetics |
| VIRAMIDINE | Nucleoside Analogue | ICN |
| ZADAXIN (thymosin alfa-1) | Immunomodulator | Sci Clone |
| CEPLENE histamine dihydrochloride | Immunomodulator | Maxim |
| VX 950/LY 570310 | Protease Inhibitor | Vertex/Eli Lilly |
| ISIS 14803 | Antisense | Isis Pharmaceutical/Elan |
| IDN-6556 | Caspase inhibitor | Idun Pharmaceuticals, Inc. http://www.idun.com |
| JTK 003 | Polymerase Inhibitor | AKROS Pharma |
| Tarvacin | Anti-Phospholipid Therapy | Peregrine |
| HCV-796 | Polymerase Inhibitor | ViroPharma/Wye |
| CH-6 | Serine Protease | Schering |
| ANA971 | Isatoribine | ANADYS |
| ANA245 | Isatoribine | ANADYS |
| CPG 10101 (Actilon) | Immunomodulator | Coley |
| Rituximab (Rituxam) | Anti-CD20 Monoclonal Antibody | Genetech/IDEC |
| NM283 (Valopicitabine) | Polymerase Inhibitor | Idenix Pharmaceuticals |
| HepX ™-C | Monclonal Antibody | XTL |
| IC41 | Therapeutic Vaccine | Intercell |
| Medusa Interferon | Longer acting interferon | Flamel Technologies |
| E-1 | Therapeutic Vaccine | Innogenetics |
| Multiferon | Long Acting Interferon | Viragen |
| BILN 2061 | Serine Protease | Boehringer - Ingelheim |
| Interferon beta-1a (REBIF) | Interferon | Ares-Serono |

VI. Combination Therapy for the Treatment of Proliferative Conditions

In another embodiment, the compounds, when used as an antiproliferative, can be administered in combination with another compound that increases the effectiveness of the therapy, including but not limited to an antifolate, a 5-fluoropyrimidine (including 5-fluorouracil), a cytidine analogue such as β-L-1,3-dioxolanyl cytidine or β-L-1,3-dioxolanyl 5-fluorocytidine, antimetabolites (including purine antimetabolites, cytarabine, fudarabine, floxuridine, 6-mercaptopurine, methotrexate, and 6-thioguanine), hydroxyurea, mitotic inhibitors (including CPT-11, Etoposide (VP-21), taxol, and vinca alkaloids such as vincristine and vinblastine, an alkylating agent (including but not limited to busulfan, chlorambucil, cyclophosphamide, ifofamide, mechlorethamine, melphalan, and thiotepa), nonclassical alkylating agents, platinum containing compounds, bleomycin, an anti-tumor antibiotic, an anthracycline such as doxorubicin and dannomycin, an anthracenedione, topoisomerase II inhibitors, hormonal agents (including but not limited to corticosteroids (dexamethasone, prednisone, and methylprednisone), androgens such as fluoxymesterone and methyltestosterone, estrogens such as diethylstilbesterol, antiestrogens such as tamoxifen, LHRH analogues such as leuprolide, antiandrogens such as flutamide, aminoglutethimide, megestrol acetate, and medroxyprogesterone), asparaginase, carmustine, lomustine, hexamethyl-melamine, dacarbazine, mitotane, streptozocin, cisplatin, carboplatin, levamasole, and leucovorin. The compounds of the present invention can also be used in combination with enzyme therapy agents and immune system modulators such as an interferon, interleukin, tumor necrosis factor, macrophage colony-stimulating factor and colony stimulating factor.

VII. Process for the Preparation of Active Compounds

The following synthetic methods and schemes provide an understanding of the method of the present invention. These schemes are of illustrative purpose, and are not meant to limit the scope of the invention. Equivalent, similar, or suitable solvents, reagents or reaction conditions may be substituted for those particular solvents, reagents, or reaction conditions described herein without departing from the general scope of the method of synthesis.

2'-Deoxy-2'-fluoronucleoside phosphonates II ($R^1$=H, X=O, S) are synthesized by adopting Kim's method (see Kim et al., J. Org. Chem. 1991, 56, 2642). The key intermediates furanoid glycals 3 are prepared from 2'-deoxy nucleosides 1 utilizing Horwitz method (see Zemlicka et al., J. Am. Chem. Soc. 1972, 94, 3213). From the glycals 3, the (dimethylphosphono)methoxy functionality is introduced either through phenylselenyl chloride addition followed by substitution with dimethyl (hydroxymethyl)phosphonate in the presence of silver perchlorate, or directly with the aid of N-(phenylseleno)phthalimide or iodine bromide. Elimination of phenylselenyl or iodo groups results in the formation of the double bond products 5, which give rise to ribonucleosides 6 upon oxidation. The 2'-down hydroxyl group of compounds 6 are converted to arabinol nucleosides 8 by selective protection of 3'-hydroxy followed by oxidation-reduction procedure (see Nguyen-Trung, et al., J. Org. Chem. 2003, 68, 2038-2041). Alternatively, if the base is pyrimidine, the conversion is achieved by 2,2'-anhydro formation followed by hydrolysis. Through a means of fluorination, including those method involving 2'-sulfonate intermediates or direct fluorination using DAST or Deoxyfluoro, 2'-arabinol nucleosides 8 are transformed to 2'-deoxy-2'-fluoro compounds 9. Final de-protection of 9 gives the 2'-fluoronucleoside phosphonates II, as depicted in Scheme 1.

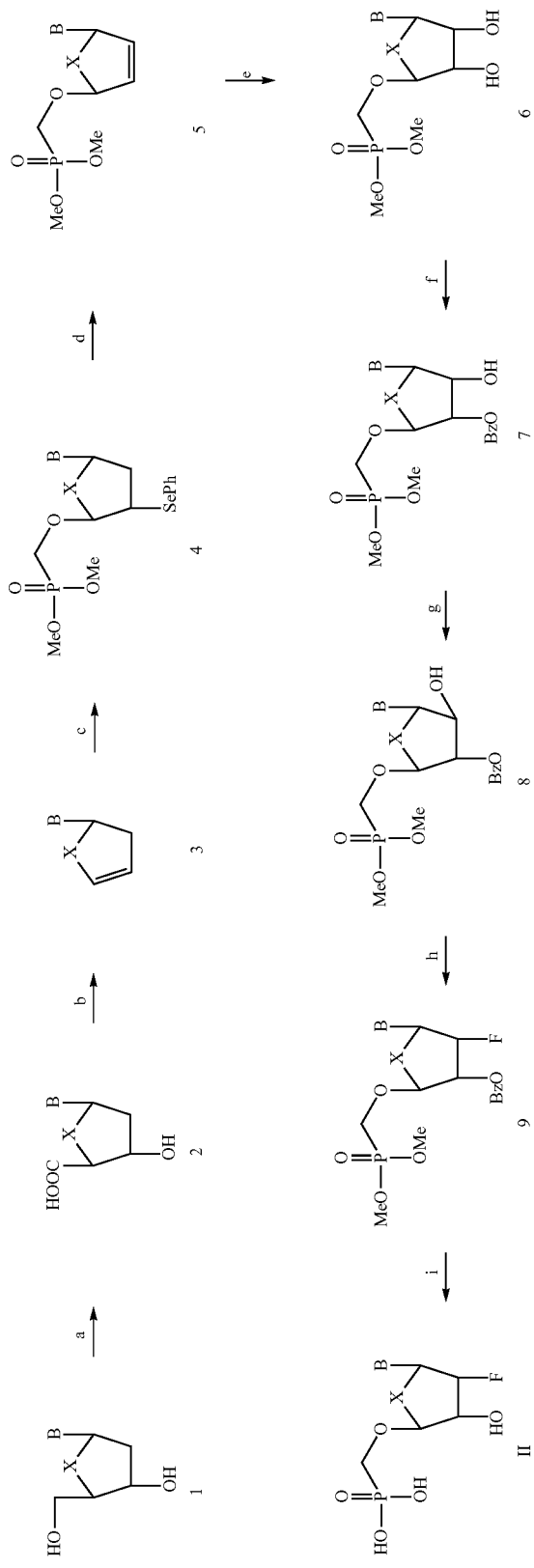

Scheme 1. Synthesis of 2′-deoxy-2′-fluoronucleoside phosphonates II ($R^1$ = H, X = O, S).

Reagents and conditions: X = O, S; B = protected or unprotected purine and pyrimidine base; (a) Pt, pH 9 or $CrO_3$, Py or $KMnO_4$; (b) DMF, dimethylformamide dineopentyl acetal, 80-90° C.; (c) i) PhSeCl, -70° C.; ii) $AgClO_4(MeO)_2P(=O)CH_2OH$; or N-(phenylseleno)phthalimide, $(MeO)_2P(=O)CH_2OH$; (d) $NaIO_4$; (e) $OsO_4$; (f) BzCl, Py; (g) B = pyrimidine: i) MsCl, Py; ii) $NH_4OH$; B = purine: i) $CrO_3$, $Ac_2O$, Py; ii) $NaBH_4$; (h) DAST, $CH_2Cl_2$; (i) $NH_3$—MeOH; ii) TMSBr.

Because of the stability of 4'-hydroxy carbocyclic nucleosides, the carbocyclic nucleosides 11 are prepared directly from cyclopentenol ester 10 via Trost reaction. By adopting similar methods as described in Scheme 1, the 2'-fluoro functionality is introduced in carbocyclic nucleosides. The substitution of 17 with (EtO)(OH)P(=O)CH$_2$OTs followed by deprotection results in the carbocyclic 2'-fluoronucleoside phosphonates II (R$^1$=H, X=CH$_2$), as depicted in Scheme 2.

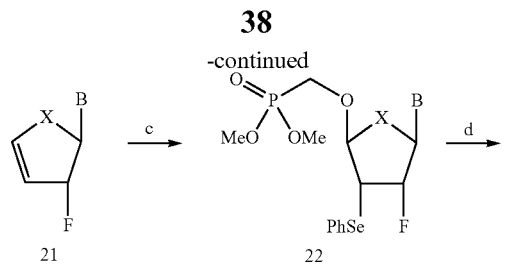

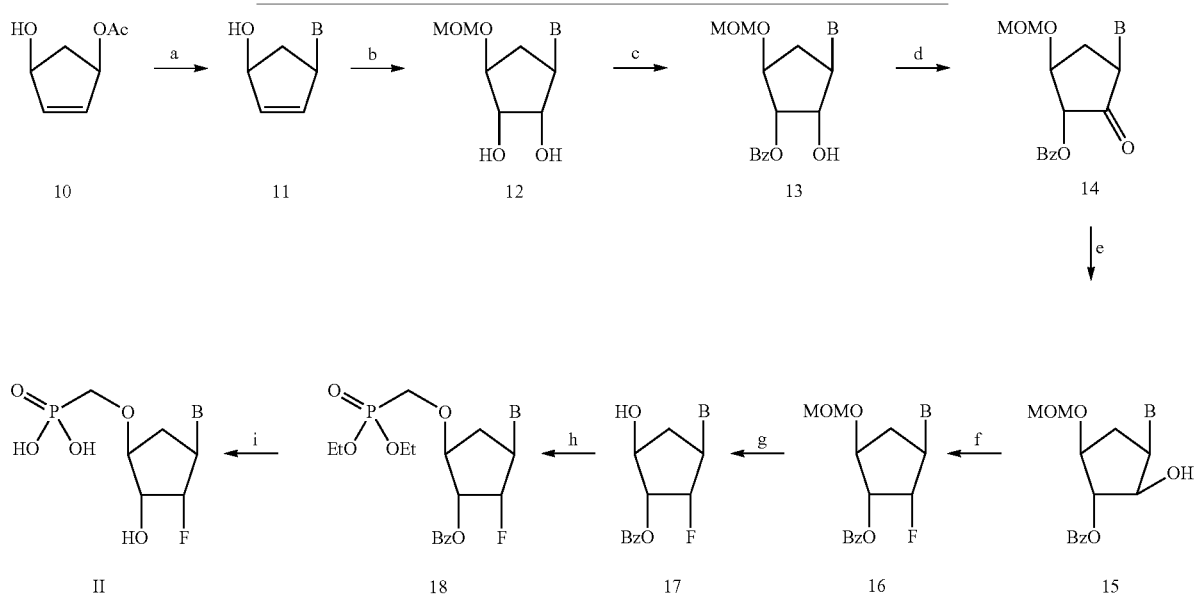

Scheme 2. Synthesis of carbocyclic 2'-fluoronucleoside phosphonates II (R$^1$ = H, X = CH$_2$).

Reagents and conditions: (a) Pd(PPh$_3$)$_4$, PPh$_3$, NaH, Base; (b) i) CH$_2$(OMe)$_2$, CH$_2$Cl$_2$, TfOH; ii) OsO$_4$; (c) BzCl, Py; (d) CrO$_3$; (e) NaBH$_4$; (f) DAST; (g) CF$_3$COOH, CH$_2$Cl$_2$; (h) (EtO)(HO)P(=O)CH$_2$OTs, NaH; (i) i) NH$_3$, MeOH; ii) TMSBr.

The strategy of introducing dimethyl(hydroxymethyl) phosphonate (Kim's method) is used for the synthesis of 2'-fluoro-2',3'-didehydro-2',3'-dedeoxy-nucleoside phosphonates IV (X=O, S). Thus, 2'-deoxy-2'-fluoronucleosides 19 are converted to glycals 21 through oxidation and elimination. Addition of dimethyl (hydroxymethyl)phosphonate followed by elimination and deprotection gives rise to the 2'-fluoro-d4 nucleoside phosphonates IV (X=O, S) (Scheme 3).

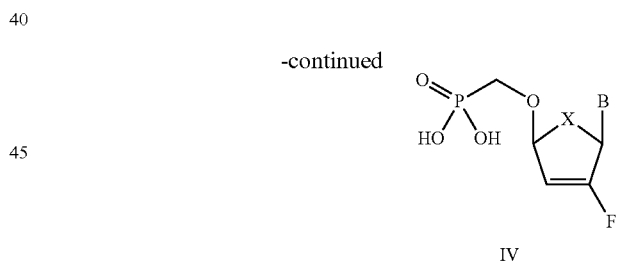

Reagents and conditions: X = O, S; B = protected or unprotected purine and pyrimidine base; (a) Pt, pH 9 or CrO$_3$, Py or KMnO$_4$; (b) DMF, dimethylformamide dineopentyl acetyl, 80-90° C.; (c) i) PhSeCl, -70° C.; ii) AgClO$_4$, (MeO)$_2$P(=O)CH$_2$OH; or N-(phenylseleno) phthalimide, (MeO)$_2$P(=O)CH$_2$OH; (d) i) NaIO$_4$; ii) TMSBr.

Scheme 3. Synthesis of 2',3'-didehydro-2',3'-dideoxy-2'-fluoronucleoside phosphonates IV (X = O, S).

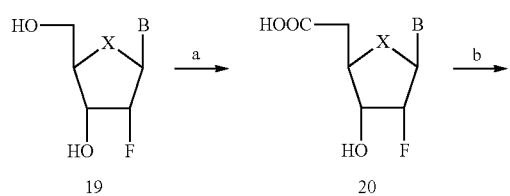

Carbocyclic 2'-fluoro-2',3'-didehydro-2',3'-dideoxy-nucleoside phosphonates IV (X=CH$_2$) are synthesized from 2-fluoro-cyclopentendiol 31. From cyclopentendiol 23, after acetonization, epoxidation, ring-opening, and oxidation, ketone 28 is prepared. Subjected to fluorination with DAST followed by elimination and deprotection, 2-fluoro-cyclopentendiol 31 is formed. After acetylation, Trost reaction, substitution with (EtO)$_2$P(=O)CH$_2$OTs, and deprotection, carbocyclic 2'-fluoro-d4 nucleoside phosphonates IV (X=CH$_2$) are furnished (Scheme 4).

Scheme 4. Synthesis of carbocyclic 2′,3′-dideoxy-2′,3′-didehydro-2′-fluoronucleoside phosphonates IV (X = CH$_2$).

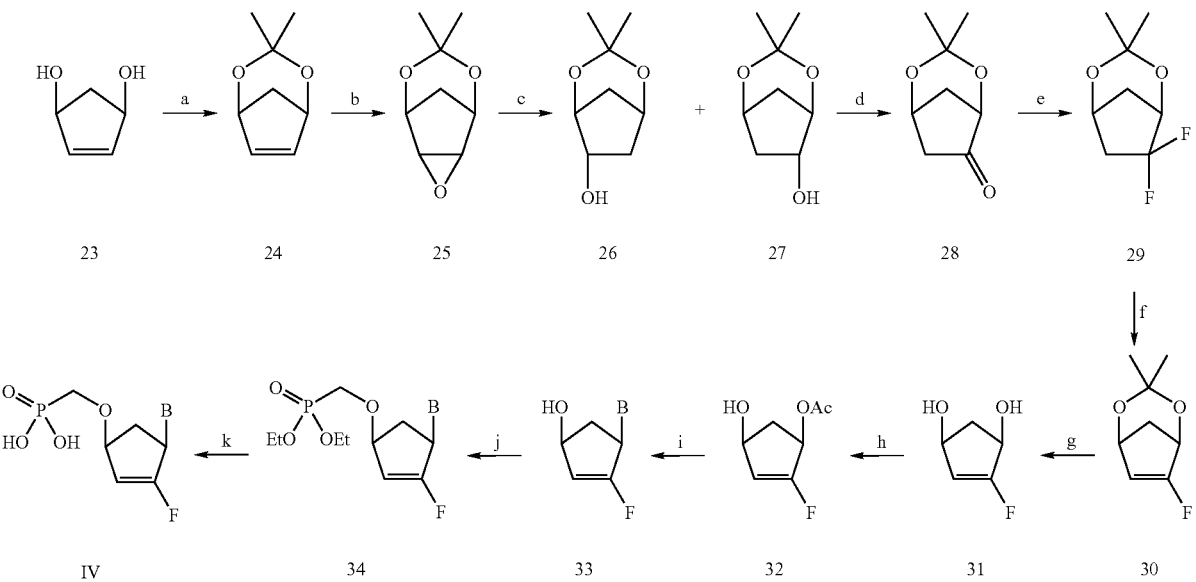

Reagents and conditions: B = protected or unprotected purine and pyrimidine base; (a) Acetone, H$_2$SO$_4$, CuSO$_4$; (b) m-CPBA; (c) LiAlH$_4$; (d) CrO$_3$; Ac$_2$O, CH$_2$Cl$_2$, Py; (e) DAST; (f) t-BuOK; (g) CF$_3$COOH; (h) Ac$_2$O, Py; (i) Pd(PPh$_3$)$_4$, PPh$_3$, NaH, Base; (j) (EtO)$_2$P(═O)CH$_2$OTs, NaH; (k) TMSBr.

For the synthesis of 2′-deoxy-2′-fluoro-2′-methyl-nucleoside phosphonates II ($R^1$═CH$_3$), the ribonucleoside phosphonates 7 are oxidized to ketones 35. Addition of MeLi or MeMgI to the ketones 35, followed by fluorination with DAST, 2′-fluoro-2′-methyl compounds 37 are prepared. Upon deprotection, the 2′-deoxy-2′-fluoro-2′-methyl-nucleoside phosphonates II ($R^1$═CH$_3$) are obtained (Scheme 5).

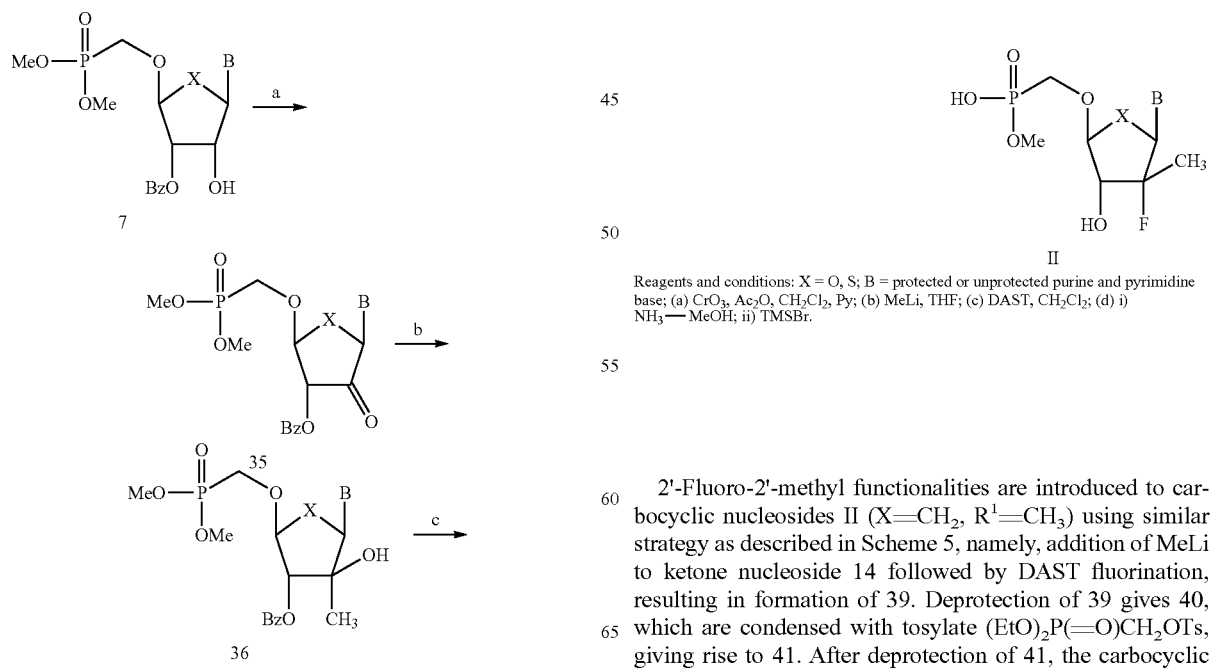

Reagents and conditions: X = O, S; B = protected or unprotected purine and pyrimidine base; (a) CrO$_3$, Ac$_2$O, CH$_2$Cl$_2$, Py; (b) MeLi, THF; (c) DAST, CH$_2$Cl$_2$; (d) i) NH$_3$—MeOH; ii) TMSBr.

2′-Fluoro-2′-methyl functionalities are introduced to carbocyclic nucleosides II (X═CH$_2$, $R^1$═CH$_3$) using similar strategy as described in Scheme 5, namely, addition of MeLi to ketone nucleoside 14 followed by DAST fluorination, resulting in formation of 39. Deprotection of 39 gives 40, which are condensed with tosylate (EtO)$_2$P(═O)CH$_2$OTs, giving rise to 41. After deprotection of 41, the carbocyclic analogs II (X═CH$_2$, $R^1$═CH$_3$) are obtained (Scheme 6).

Scheme 6. Synthesis of carbocyclic 2'-deoxy-2'-methyl-2'-fluoronucleoside phosphonates II (X = CH$_2$, R$^1$ = CH$_3$).

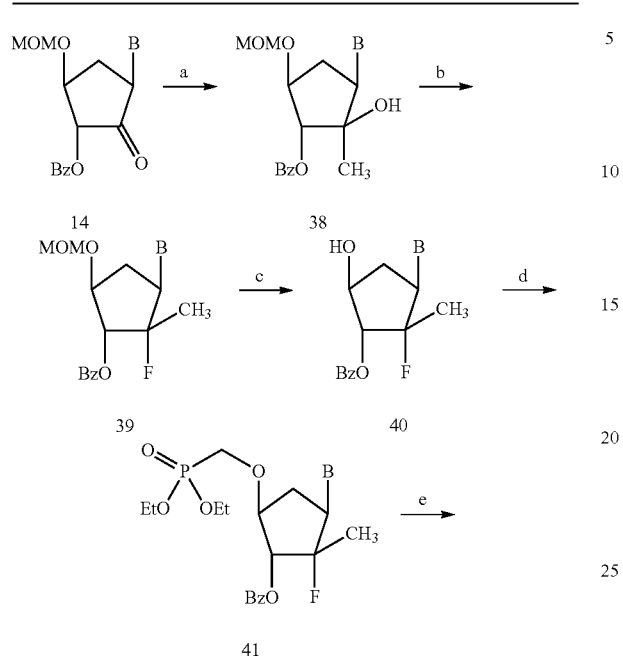

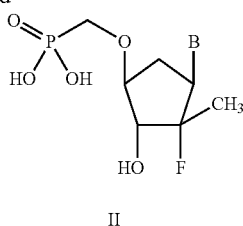

Reagents and conditions: B = protected or unprotected purine and pyrimidine base; (a) MeLi, THF; (b) DAST, CH$_2$Cl$_2$; (c) CF$_3$COOH, CH$_2$Cl$_2$; (d) (EtO)$_2$P(=O)CH$_2$OTs, NaH; (e) i) NH$_3$, MeOH; ii) TMSBr.

Alternatively, Cook's method is also used for the preparation of 2'-deoxy-2'-fluoro-2'-methyl-pyrimidine nucleoside phosphonates II (B=pyrimidine). Thus, uridine analog 42 is silylated at 5'-position. Benzoylation and N-protection, followed by desilylation result in 44, which are oxidized and substituted by acetoxyl, giving rise to 46. Addition of diethyl (hydroxymethyl)phosphonate followed by deprotection convert 46 to uridine analog 48. Through amination and deprotection, the cytidine analog II (X=O, S) is prepared (Scheme 7).

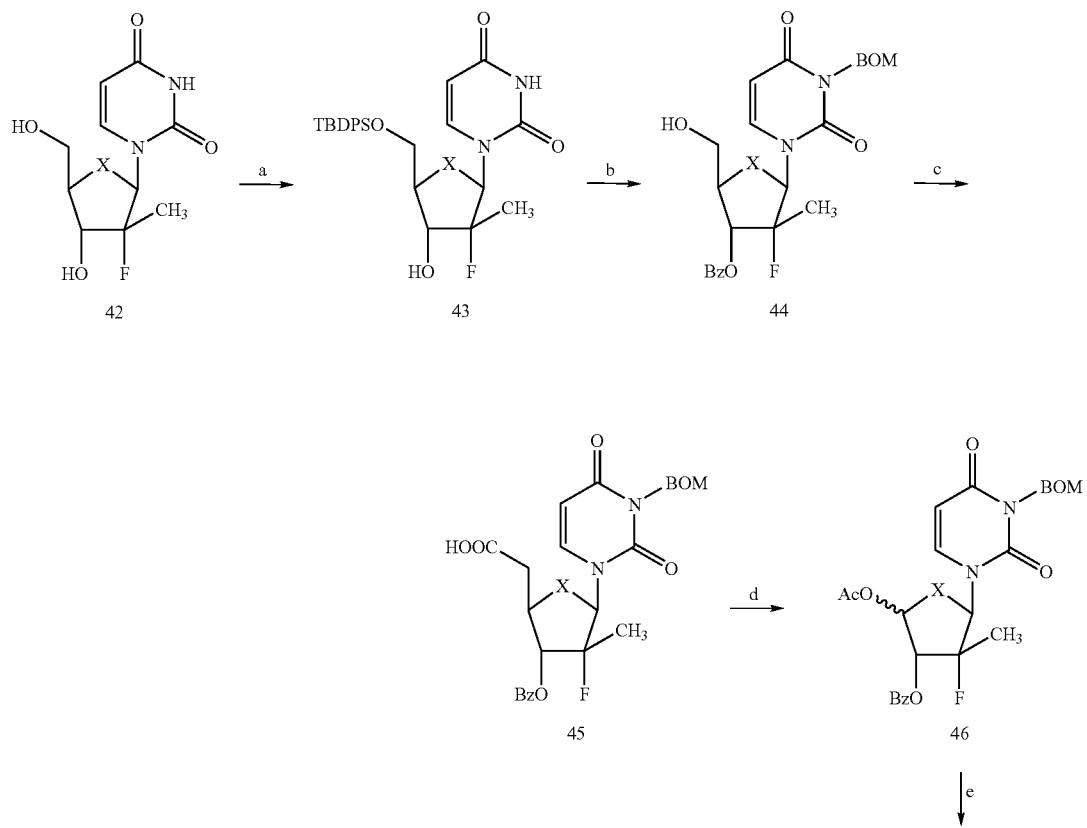

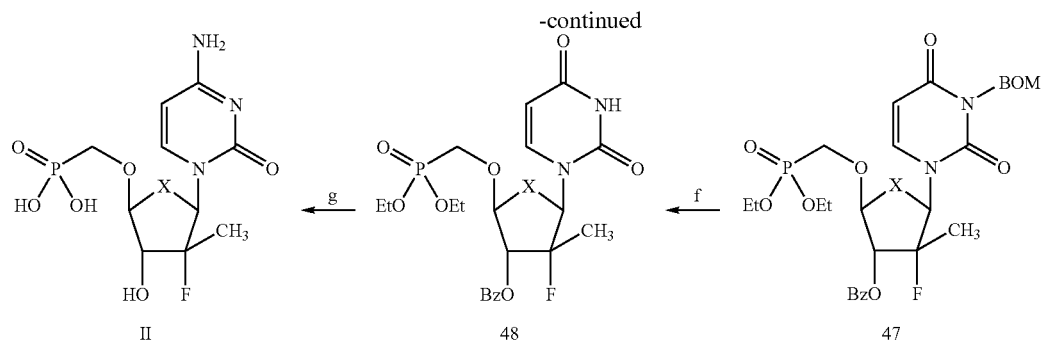

Reagents and conditions: X = O, S; (a) TBDPSCl, DMF, imidazole; (b) i) BOMCl, (i-Pr)₂NEt, CH₂Cl₂; ii) BzCl, Py; iii) TBAF, THF; (c) i) CrO₃, Ac₂O, Py, CH₂Cl₂, T-BuOH, DMF; ii) CF₃COOH; (d) Pb(OAc)₄, Py, DMF; (e) (EtO)₂P(=O)CH₂OH, TMSOTf, CH₂Cl₂; (f) H₂, Pd(OH)₂, MeOH, acetone; (g) i) (i-Pr)₃C₆H₂SO₂Cl, THF; ii) NH₄OH; iii) TMSBr.

5'-Deoxynucleoside phosphonates I and III are synthesized respectively from 5'-iodo compounds 51 and 55, which are prepared from corresponding nucleosides 49 and 53 via tosylation and iodination, or direct iodination with triphenylphosphine and iodine. Substitution of the iodo compounds 51 and 55 with triethyl phosphate, followed by deprotection, 2'-fluoronucleoside phosphonates I and III are obtained (Scheme 8). This method has been used widely for the synthesis of 5'-deoxynucleoside phosphonates (see Holy, et al., Tetrahedron Lett. 1967, 881-884).

Scheme 8. Synthesis of 5'-deoxy-2'-fluoronucleoside phosphonates I and III (n = 1).

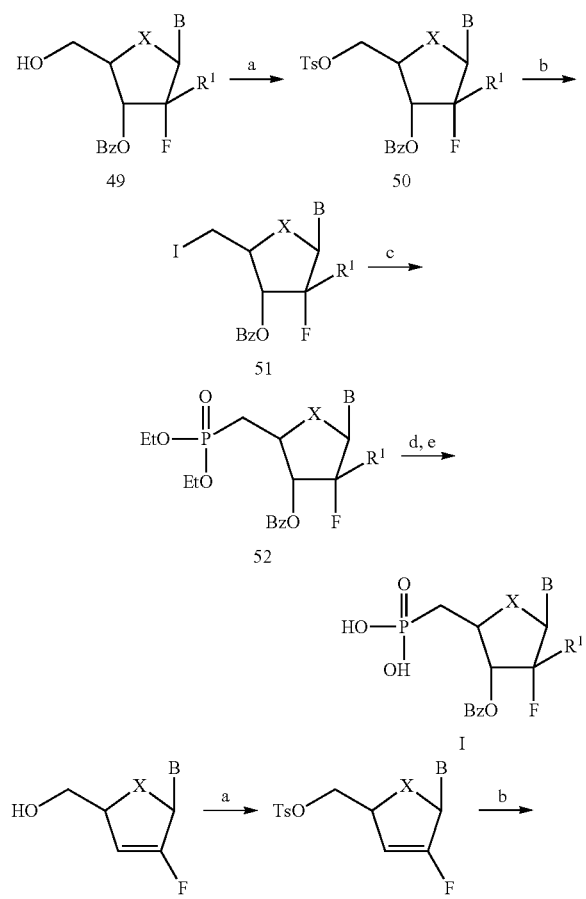

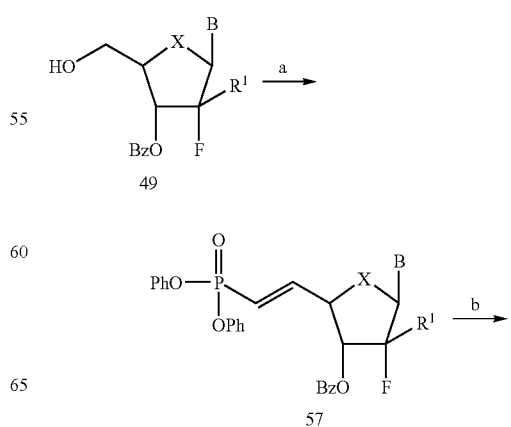

Reagents and conditions: X = O, S, CH₂; R¹ = H or CH₃; B = protected or unprotected purine or pyrimidine; (a) TsCl, Py; (b) NaI, EtCOMe; (c) (EtO)₃P; (d) NH₃, MeOH; (e) TMSBr.

The 5'-methylene phosphonates I are synthesized from nucleosides 49 by adapting a published procedure (see Koh, et al., J. Med. Chem. 2005, 48, 2867-2875), which involved oxidation, Wittig reaction, and reduction. The d4 analogs III are synthesized by condensation of iodo compounds 59 with diethyl lithiomethane phosphonate, followed by deprotection, a method used by Wolff-Kugel and Halazy (Wolff-Kungel, Halazy, Tetrahedron Lett. 1991, 32, 6341-6344). These procedures are depicted in Scheme 9.

Scheme 9. Synthesis of 5'-methylene-2'-fluoronucleoside phosphonates I and III (n = 2).

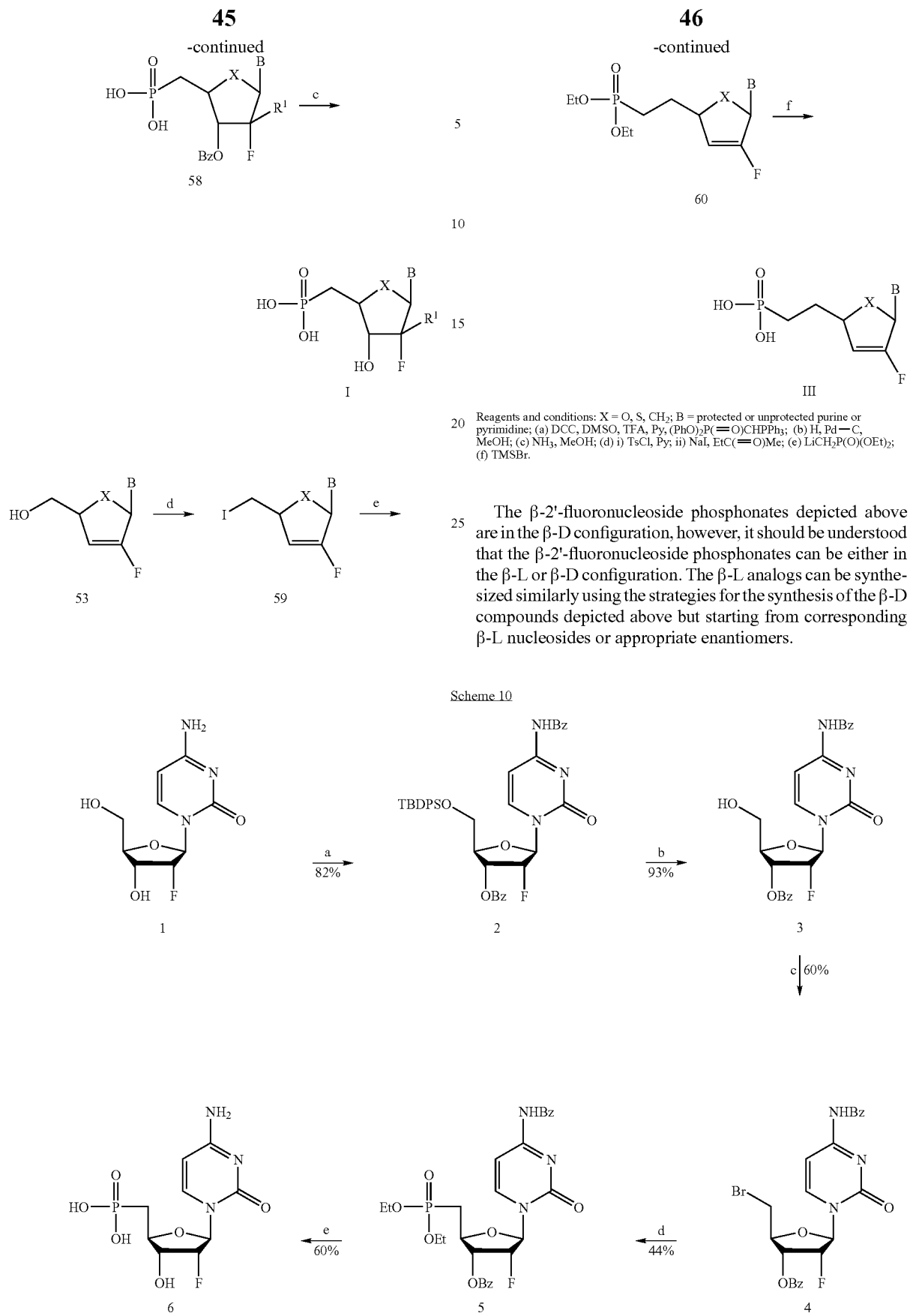

Reagents and conditions: X = O, S, CH$_2$; B = protected or unprotected purine or pyrimidine; (a) DCC, DMSO, TFA, Py, (PhO)$_2$P(=O)CHPPh$_3$; (b) H, Pd—C, MeOH; (c) NH$_3$, MeOH; (d) i) TsCl, Py; ii) NaI, EtC(=O)Me; (e) LiCH$_2$P(O)(OEt)$_2$; (f) TMSBr.

The β-2'-fluoronucleoside phosphonates depicted above are in the β-D configuration, however, it should be understood that the β-2'-fluoronucleoside phosphonates can be either in the β-L or β-D configuration. The β-L analogs can be synthesized similarly using the strategies for the synthesis of the β-D compounds depicted above but starting from corresponding β-L nucleosides or appropriate enantiomers.

Scheme 10

Synthesis of 2-Fluoro-2-deoxy-phosphonylcytidine. Reagents and reaction conditions:

a) i. TBDPSCl, DMAP, $Et_3N$, DMF, 50-60° C.; ii. BzCl, pyridine, rt, 12 h; b) TBAF, THF, rt, 6 h; c) $PPh_3$, $CBr_4$, $CH_2Cl_2$, rt, 48 h; d) $(EtO)_3P$, 140° C., 24 h; e) i. TMSBr, $CH_3CN$, 0° C.→rt, 12 h; ii. $NH_3$/MeOH, 30° C., 12 h.

Synthesis of (2R,3R,4S,5R)-5-(4-Benzamido-2-oxopyrimidin-1(2H)-yl)-2-((tert-butyldiphenylsilyloxy)methyl)-4-fluoro-tetrahydrofuran-3-yl benzoate (2)

To a solution of 2-deoxy-2-fluorocytidine (0.32 g, 1.32 mmol) and DMAP (0.32 g, 2.60 mmol) in 5.0 mL of anhydrous DMF was added $Et_3N$ (0.27 mL, 1.95 mmol) and TBDPSCl (0.50 mL, 1.96 mmol) at 0° C. under $N_2$ atmosphere. The resulting solution was stirred for 12 h at 50° C. and treated with MeOH (0.5 mL) at rt. After stirring the solution additionally, the solvent was removed under reduced pressure. The residue was dried under high vacuum for 24 h at room temperature. The crude product was dissolved in 10 mL of anhydrous pyridine at 0° C. under $N_2$ atmosphere. To the solution was added to benzoyl chloride (0.4 mL, 3.40 mmol). After stirring the solution at rt for 12 h, the solution was treated with MeOH (1.0 mL) at rt. The solution was concentrated in vacuo and the residue was purified on silica gel column chromatography (Hexane:EtOAc=2:1 to 1:2 v/v) to give compound 2 (0.64 g, 0.92 mmol) in 82% yield. $^1$H NMR ($CDCl_3$, 400 MHz) δ 9.31 (br, 1H), 8.45 (d, J=8.0, 1H), 7.96 (m, 4H), 7.66-7.37 (m, 15H), 7.18 (m, 2H), 6.26 (d, J=16.0, 1H), 5.50 (m, 1H), 5.48 (d, J=3.5, 0.5H), 5.34 (d, J=3.5, 0.5H), 4.52 (d, J=8.8, 1H), 4.28 (dd, J=12.0, 1.6, 1H), 3.87 (dd, J=12.0, 1.6, 1H), 1.10 (s, 9H); MS calcd for $C_{39}H_{38}FN_3O_6Si$ m/z 692.3 (M+H)$^+$, found 692.4.

Synthesis of (2R,3R,4S,5R)-5-(4-Benzamido-2-oxopyrimidin-1(2H)-yl)-4-fluoro-2-(hydroxymethyl)-tetrahydrofuran-3-yl benzoate (3)

To a solution of compound 2 (0.64 g, 0.92 mmol) in 10.0 mL of anhydrous THF was added TBAF (1.20 mL, 1.0 M in THF) at 0° C. The resulting solution was stirred for 6 h at rt. The solvent was removed under reduced pressure and the residue was purified on silica gel column chromatography (Hexane:EtOAc=4:1 to 1:1 v/v) to give compound 3 (0.39 g, 0.85 mmol) in 93% yield. $^1$H NMR ($CD_3OD$, 400 MHz) δ 8.58 (d, J=7.6, 1H), 8.00 (m, 4H), 7.63 (m, 3H), 7.51 (m, 4H), 6.16 (dd, J=17.6, 1.6, 1H), 5.55 (dd, J=4.4, 1.6, 0.5H), 5.47 (m, 1H), 5.42 (dd, J=4.4, 1.6, 0.5H), 4.51 (m, 1H), 4.06 (dd, J=12.8, 2.4, 1H), 3.86 (dd, J=12.8, 3.2, 1H); MS calcd for $C_{23}H_{20}FN_3O_6$ m/z 454.1 (M+H)$^+$, found 454.2.

Synthesis of (2S,3R,4S,5R)-5-(4-Benzamido-2-oxopyrimidin-1(2H)-yl)-2-(bromomethyl)-4-fluoro-tetrahydrofuran-3-yl benzoate (4)

To a solution of compound 3 (0.12 g, 0.27 mmol) and $CBr_4$ (0.11 g, 0.33 mmol) in 5.0 mL of anhydrous $CH_2Cl_2$ was added $PPh_3$ (0.12 g, 0.41 mmol) at 0° C. under $N_2$ atmosphere. The resulting solution was stirred for 48 h at room temperature. The solvent was removed under reduced pressure and the residue was purified on silica gel column chromatography (Hexane:EtOAc=1:2 to 1:4 v/v) to give compound 4 (0.08 g, 0.16 mmol) in 60% yield. $^1$H NMR ($CDCl_3$, 400 MHz) δ 8.95 (br, 1H), 8.14 (d, J=7.6, 1H), 8.05 (d, J=7.2, 2H), 7.92 (d, J=7.2, 2H), 7.62 (m, 3H), 7.52 (d, J=7.6, 1H), 7.48 (m, 3H), 6.06 (dd, J=15.2, 1.2, 1H), 5.63 (d, J=4.8, 1.2, 0.5H), 5.50 (dd, J=4.8, 1.2, 0.5H), 5.44 (m, 1H), 4.68 (m, 1H), 3.92 (dd, J=12.0, 4.0, 1H), 3.77 (dd, J=12.0, 4.8, 1H); MS calcd for $C_{23}H_{19}BrFN_3O_5$ m/z 516.1 (M+H)$^+$, found 518.3.

Synthesis of (2S,3R,4S,5R)-5-(4-Benzamido-2-oxopyrimidin-1(2H)-yl)-2-((diethoxyphosphoryl)methyl)-4-fluoro-tetrahydrofuran-3-yl benzoate (5)

A solution of compound 4 (0.08 g, 0.16 mmol) in 10 mL of $(EtO)_3P$ was stirred at 140° C. for 24 h and the solvent was evaporated under reduced pressure. The residue was dissolved in 10 mL of MeOH and adsorbed on silica gel and then purified on silica gel column chromatography (Hexane:EtOAc=1:2 to 1:4 v/v) to give compound 5 (0.04 g, 0.07 mmol) in 44% yield. $^1$H NMR ($CDCl_3$, 400 MHz) δ 8.97 (br, 1H), 8.08 (d, J=7.2, 2H), 8.04 (d, J=7.6, 1H), 7.92 (d, J=7.2, 2H), 7.60 (m, 3H), 7.50 (m, 4H), 5.98 (d, J=18.4, 1H), 5.65 (d, J=4.8, 0.5H), 5.52 (d, J=4.8, 0.5H), 5.45 (m, 1H), 4.76 (m, 1H), 4.11 (m, 4H), 2.42 (m, 2H), 1.32 (m, 6H); MS calcd for $C_{27}H_{29}FN_3O_8P$ m/z 574.2 (M+H)$^+$, found 574.3.

Synthesis of ((2S,3S,4S,5R)-5-(4-Amino-2-oxopyrimidin-1(2H)-yl)-4-fluoro-3-hydroxy-tetrahydrofuran-2-yl)methylphosphonic acid (6)

Compound 5 (0.03 g, 0.05 mmol) in anhydrous $CH_3CN$ was treated with TMSBr (0.02 g, 0.13 mmol) at 0° C. under argon atmosphere. The resulting solution was stirred for 3 h at rt. The volatiles were removed under reduced pressure, and then the residue was dissolved in 50 mL of methanolic ammonia solution and heated in a steel bomb at 30° C. for 12 h. The solution was concentrated under reduced pressure, and the residue was purified on reverse phase $C_{18}$ liquid chromatography ($H_2O$ to $CH_3CN$, gradient) to give compound (0.01 g, 0.032 mmol) in 60% yield. $^1$H NMR ($CD_3OD$ 400 MHz) δ 8.00 (d, J=8.0, 2H), 6.05 (d, J=8.0, 1H), 5.83 (d, J=19.2, 1H), 5.11 (dd, J=12.8, 4.0, 1H), 4.20 (m, 1H), 4.01 (m, 1H), 2.24 (m, 1H), 2.13 (m, 1H); MS calcd for $C_9H_{13}FN_3O_6P$ m/z 310.1 (M+H)$^+$, found 310.1.

VIII. Biological Activity

Anti-HIV (in PBM Cells) Assay

Anti-HIV-1 activity of the compounds was determined in human peripheral blood mononuclear (PBM) cells as described previously (Schinazi R. F., McMillan A., Cannon D., Mathis R., Lloyd R. M. Jr., Peck A., Sommadossi J.-P., St. Clair M., Wilson J., Furman P. A., Painter G., Choi W.-B., Liotta D. C. Antimicrob. Agents Chemother. 1992, 36, 2423; Schinazi R. F., Sommadossi J.-P., Saalmann V., Cannon D., Xie M.-Y., Hart G., Smith G., Hahn E. Antimicrob. Agents Chemother. 1990, 34, 1061). Stock solutions (20-40 mM) of the compounds were prepared in sterile DMSO and then diluted to the desired concentration in growth medium. Cells were infected with the prototype HIV-$1_{LAI}$ at a multiplicity of infection of 0.01. Virus obtained from the cell supernatant was quantified on day 6 after infection by a reverse transcriptase assay using $(rA)_n \cdot (dT)_{12-18}$ as template-primer. The DMSO present in the diluted solution (<0.1%) had no effect on the virus yield. AZT was included as positive control. The antiviral $EC_{50}$ and $EC_{90}$ were obtained from the concentration-response curve using the median effective method described previously (Chou T.-C. & Talalay P. *Adv. Enzyme Regul.* 1984, 22, 27-55; Belen'kii M. S. & Schinazi R. F. *Antiviral Res.* 1994, 25, 1-11).

Anti-HBV Assay

The anti-HBV activity of the compounds can be determined by treating the AD-38 cell line carrying wild type HBV under the control of tetracycline (Ladner S. K., Otto M. J., Barker C. S., Zaifert K., Wang G. H., Guo J. T., Seeger C. &

King R. W. Antimicrob. Agents Chemother. 1997, 41, 1715-1720). Removal of tetracycline from the medium [Tet (-)] results in the production of HBV. The levels of HBV in the culture supernatant fluids from cells treated with the compounds can be compared with that of the untreated controls. Control cultures with tetracycline [Tet (+)] can be also maintained to determine the basal levels of HBV expression. 3TC can be included as positive control.

Anti-HCV Assay

The compound was dissolved in DMSO and added to the culture media at final concentrations ranging from 1 to 100 µM. A 4-days incubation resulted in dose-dependant reduction of the replicon HCV RNA. Since 3.3 Ct values equals 1-log reduction of replicon RNA, an $EC_{90}$ value was calculated. Further analysis of the reduction of cellular DNA levels (ribosomal DNA) or cellular RNA levels (ribosomal RNA) resulted in a $\Delta Ct$ that expressed the inhibitory capacity of this compound on host DNA and RNA polymerases. Subtraction of these cellular $\Delta Ct$ values from the antiviral $\Delta Ct$ values resulted in the therapeutic index $\Delta\Delta Ct$ values. Based on these calculations, an average $EC_{90}$ value, corrected for cellular toxicity, was obtained.

HCV Polymerase Expression and Purification

The HCV NS5B gene was amplified from a genotype 1A, clone, p134/pBRTM 2029-3011 ($\Delta$AvrII). The primers used added a methionine and alanine to the N terminus and truncated the C terminal 21 amino acids, replacing them with a hexahistidine tag, which allowed increased soluble product in E. coli and metal affinity purification. The PCR product was cloned into the pET32a expression construct (Novagen) at the Nco1 and BamH1 sites and the resultant plasmid (pRSK1) was sequenced by the Stanford PAN facility using standard methods. BL1(DE3)pLysS cells (Novagen) were transformed by pRSK1 and grown at 37° C. to an optical density of 0.1, at which time the cells were switched to room temperature. At an optical density of 0.3-0.5, isopropyl-β-D-thiogalactopyanoside was added to a final concentration of 0.5 mM and the cells were harvested after 6 h. The cell pellet was frozen, thawed and resuspended in buffer containing 50 mM sodium phosphate pH 7.0, 10% glycerol, 0.3 M NaCl, 2 mM β-mercaptoethanol, 0.5% β-octyl-glucoside. The cell extract was sonicated, and cellular debris removed by centrifugation. The extract was incubated batch-wise with Talon metal affinity resin (Clontech), washed extensively with the above buffer, and then poured into a column for a stepwise imidazole elution. The polymerase, referred to as NS5Bt, eluted specifically between 70 mM and 250 mM imidazole and was ~90% pure.

HCV Polymerase Inhibition Assay

RdRp assays were a modification of the assays described in Kao et al (Kao, C, C.; Yang, X.; Kline, A.; Wang, Q. M.; Barket, D.; Heinz, B. A. (2000) J. Virol. 74, 11121-11128). The template used allows for de novo synthesis and has its 3' termini blocked by puromycin which largely prevents the high molecular weight product from forming and allows for the predominately 24 and 25 nucleotide products to be seen. Each reaction contained 50 mM Hepes-NaOH pH 8.0, 0.65 µM template, 0.1 µM purified NS5Bt described above, 250 µM GTP, 5 M UTP, 0.6 µM CTP, and 1 µM [αP32] ATP, 0.5 mM MnCl2, 7 mM $MgCl_2$, 18 mM DTT, and the stated concentration of the analog. Reaction mixes were incubated at 27° C. for 45 min. Reactions were terminated by the addition of ⅕ the volume of 5× proteinase K mix (250 µg proteinase K/ml [Sigma, St Louis, Mo.], 375 mM Hepes-NaOH pH 8, 0.5% SDS, 25 mM EDTA) and incubated for 10 min 37° C. Reactions were then precipitated with isopropanol, and glycogen as a carrier, and washed twice with 70% Ethanol to remove salt. The RNA was resuspended in formamide loading buffer, heated to 65° C. for 3 min and loaded on a 20% acrylamide/7 M Urea/TBE denaturing gel and separated by electrophoresis at 50° C. Quantification of bands was performed using Phosphoimager analysis.

BVDV Inhibition Assay

One of the best characterized members of the Pestivirus genus is BVDV. BVDV and HCV share at least three common features, which are the following: (1) they both undergo IRES-mediated translation; (2) NS4A cofactor is required by their N53 serine protease; and (3) they undergo similar polyprotein processing within the non-structural region, especially at the NS5A and NS5B junction site. Therefore, the BVDV replication system can be used for the discovery of anti-Flaviviridae compounds. The compounds described herein are active against Pestiviruses, Hepaciviruses and/or Flaviviruses.

Maldin-Darby bovine kidney (MDBK) cells can be grown and maintained in a modified eagle medium (DMEM/F12; GibcoBRL), supplemented with 10% heat inactivated horse serum at 37° C. in a humidified, 5% $CO_2$, incubator. Bovine viral diarrhea virus (BVDV), strain NADL, causes a cytopathogenic effect (CPE) after infection of these cells.

MDBK-cells, grown in DMEM/F12<10% horse serum (HS), can be isolated using standard techniques using trypsin-EDTA. Cells can be seeded in a 96-well plate at $5\times10^4$ cells/well, with test compound (20 micromolar (µM) concentration) to give a total volume of 100 microliters (µL). After one hour, the media can be removed and the cells can be infected at a multiplicity of infection (MOI) of 0.02 or 0.002 in a total volume of 50 µL for 45 minutes. Thereafter, the virus can be removed and the cells can be washed twice with 100 µL of assay media. Finally, the infected cells can be incubated in a total volume of 100 µL containing the test compound at 40 or 100 µM concentration. After 22 hours, the cell supernatant can be collected by removing the cellular debris by low-speed centrifugation, and subsequently tested for the presence of virus in a quantitative manner.

Cytotoxicity Assay

The toxicity of the compounds was assessed in Vero, human PBM, CEM (human lymphoblastoid), MT-2, and HepG2 cells, as described previously (Schinazi R. F., Sommadossi J.-P., Saalmann V., Cannon D. L., Xie M.-Y., Hart G. C., Smith G. A. & Hahn E. F. Antimicrob Agents Chemother. 1990, 34, 1061-1067). Cycloheximide was included as positive cytotoxic control, and untreated cells exposed to solvent were included as negative controls. The cytotoxicity $IC_{50}$ was obtained from the concentration-response curve using the median effective method described previously (Chou T.-C. & Talalay P. Adv. Enzyme Regul. 1984, 22, 27-55; Belen'kii M. S. & Schinazi R. F. Antiviral Res. 1994, 25, 1-11).

This invention has been described with reference to its preferred embodiments. Variations and modifications of the invention, will be obvious to those skilled in the art from the foregoing detailed description of the invention. It is intended that all of these variations and modifications be included within the scope of this invention.

What is claimed is:

1. A compound having a structure consistent with formula (1) or a pharmaceutically acceptable salt thereof,

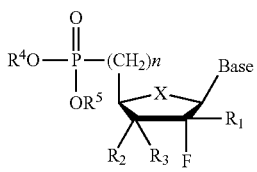

wherein:
a) X is O, S, SO$_2$, or CH$_2$;
b) n is 1 or 2;
c) R$^1$ is CH$_3$;
d) R$^2$ and R$^3$ are independently a hydrogen, halogen, OH, OR', SH, SR', N$_3$, NH$_2$, NHR', CN, OCOR', OCOOR', lower alkyl of C$_1$-C$_6$, halogenated lower alkyl of C$_1$-C$_6$, lower alkenyl of C$_2$-C$_6$, halogenated lower alkenyl of C$_2$-C$_6$, lower alkynyl of C$_2$-C$_6$, halogenated lower alkynyl of C$_2$-C$_6$, lower alkoxy of C$_1$-C$_6$ lower alkyl acid of C$_2$-C$_6$, or lower alkyl acid ester of C$_2$-C$_6$;
e) each R' is independently a hydrogen, lower alkyl of C$_1$-C$_6$, or lower cycloalkyl of C$_1$-C$_6$;
f) R$^4$ and R$^5$ are independently a hydrogen, phosphate, diphosphate, or analogs thereof wherein one or two hydrogens on a P(OH) moiety is replaced with an C$_{1-10}$ alkyl, aryl, amino acid ester, steroid, carbohydrate, or lipid group, wherein aryl groups are selected from the group consisting of phenyl, biphenyl, and naphthyl, optionally substituted with one or more moieties selected from the group consisting of hydroxyl, amino, alkylamino, arylamino, alkoxy, aryloxy, nitro, cyano, sulfonic acid, sulfate, phosphonic acid, phosphate, and phosphonate, and
g) Base is a heterocycle containing at least one nitrogen.

2. A compound having a structure consistent with formula (II) or a pharmaceutically acceptable salt thereof,

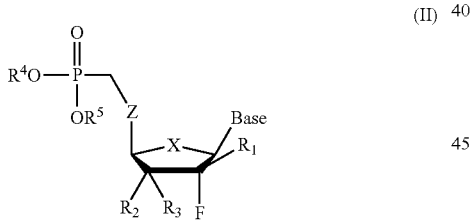

wherein:
a) X is O, S, SO$_2$, or CH$_2$;
b) Z is O, S, or NH;
c) R$^1$ is H or CH$_3$;
d) R$^2$ and R$^3$ are independently a hydrogen, halogen, OH, OR', SH, SR', N$_3$, NH$_2$, NHR', CN, OCOR', OCOOR', lower alkyl of C$_1$-C$_6$, halogenated lower alkyl of C$_1$-C$_6$, lower alkenyl of C$_2$-C$_6$, halogenated lower alkenyl of C$_2$-C$_6$, lower alkynyl of C$_2$-C$_6$, halogenated lower alkynyl of C$_2$-C$_6$, lower alkoxy of C$_1$-C$_6$, lower alkyl acid of C$_2$-C$_6$, or lower alkyl acid ester of C$_2$-C$_6$, wherein at least one of R$^2$ and R$^3$ is OH,
e) R$^4$ and R$^5$ are independently a hydrogen, phosphate, diphosphate, or analogs thereof wherein one or two hydrogens on a P(OH) moiety is replaced with an C$_{1-10}$ alkyl, aryl, amino acid ester, steroid, carbohydrate, or lipid group, wherein aryl groups are selected from the group consisting of phenyl, biphenyl, and naphthyl, optionally substituted with one or more moieties selected from the group consisting of hydroxyl, amino, alkylamino, arylamino, alkoxy, aryloxy, nitro, cyano, sulfonic acid, sulfate, phosphonic acid, phosphate, and phosphonate,
f) Base is a heterocycle containing at least one nitrogen; and
g) each R' is independently a hydrogen, lower alkyl of C$_1$-C$_6$, or lower cycloalkyl of C$_1$-C$_6$.

3. A compound having a structure consistent with formula (III) or a pharmaceutically acceptable salt thereof,

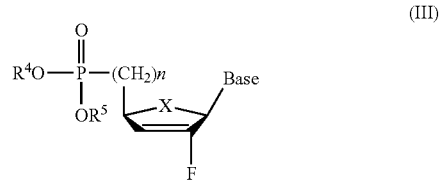

wherein:
a) X is O, S, SO$_2$, or CH$_2$;
b) n is 1 or 2;
c) R$^4$ and R$^5$ are independently a hydrogen, phosphate, diphosphate, or analogs thereof wherein one or two hydrogens on a P(OH) moiety is replaced with an C$_{1-10}$ alkyl, aryl, amino acid ester, steroid, carbohydrate, or lipid group, wherein aryl groups are selected from the group consisting of phenyl, biphenyl, and naphthyl, optionally substituted with one or more moieties selected from the group consisting of hydroxyl, amino, alkylamino, arylamino, alkoxy, aryloxy, nitro, cyano, sulfonic acid, sulfate, phosphonic acid, phosphate, and phosphonate; and
d) Base is a heterocycle containing at least one nitrogen.

4. The compound of claim 2 comprising a 2'-fluoronucleoside phosphonate of the formula:

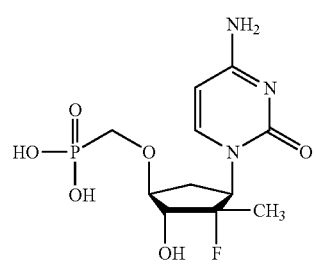

or a pharmaceutically acceptable salt thereof.

5. The compound of claim 1 comprising a 2'-fluoronucleoside phosphonate of the formula:

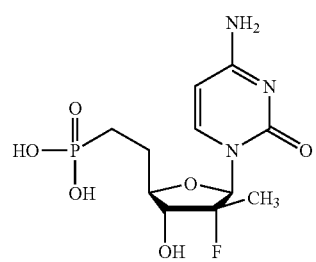

or its pharmaceutically acceptable salt.

6. The compound of claim 1 comprising a 2'-fluoronucleoside phosphonate of the formula:

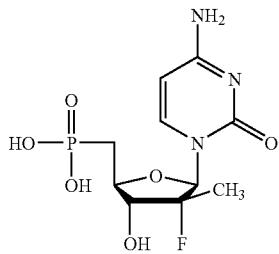

or a pharmaceutically acceptable salt thereof.

7. The compound of claim 3 comprising a 2'-fluoronucleoside phosphonate of the formula:

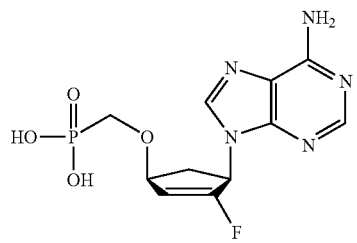 [SMILES: Nc1ncnc2c1ncn2[C@@H]1C[C@H](OCP(=O)(O)O)C=C1F]

or a pharmaceutically acceptable salt thereof.

8. The compound of claim 3 comprising a 2'-fluoronucleoside phosphonate of the formula:

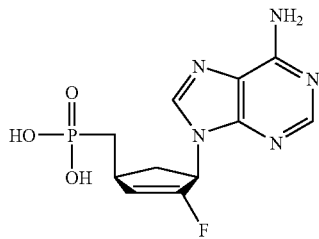 [SMILES: Nc1ncnc2c1ncn2[C@@H]1C[C@H](CP(=O)(O)O)C=C1F]

or a pharmaceutically acceptable salt thereof.

9. The compound of claim 3 comprising a 2'-fluoronucleoside phosphonate of the formula:

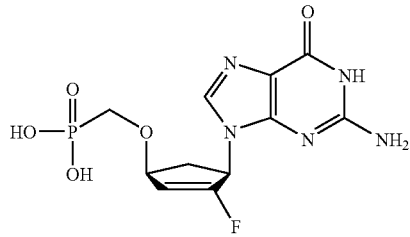

or a pharmaceutically acceptable salt thereof.

10. The compound of claim 3 comprising a 2'-fluoronucleoside phosphonate of the formula:

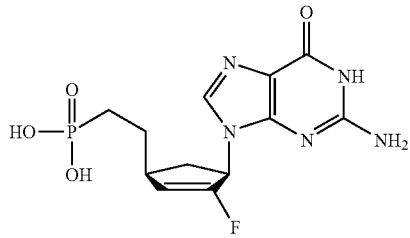 [SMILES: Nc1nc2c(ncn2[C@@H]2C[C@H](CCP(=O)(O)O)C=C2F)c(=O)[nH]1]

or a pharmaceutically acceptable salt thereof.

11. A pharmaceutical composition comprising the compound of claim 1 or 3 and at least one of a pharmaceutically acceptable carrier, diluent, vehicle, and excipient.

12. The pharmaceutical composition of claim 11 further comprising a compound selected from the group consisting of cytokines, protease inhibitors, antiviral agents, proteases, caspase inhibitors, antibodies and protease inhibitors.

13. A method of treating a viral infection, or a symptom thereof in a subject in need thereof comprising administering to the subject an effective amount the composition of claim 11.

14. The pharmaceutical composition of claim 11, further comprising at least one of an enzyme therapy agent and an immune system modulator.

15. A compound having a structure consistent with formula (II) or a pharmaceutically acceptable salt thereof,

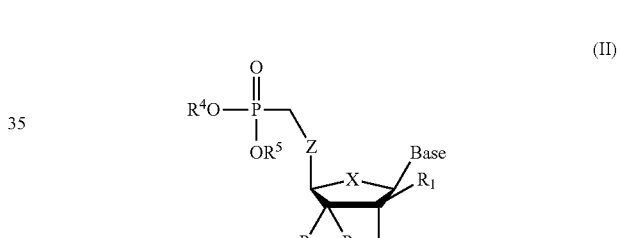

wherein:
a) X is O, S, SO$_2$, or CR$_2$;
b) Z is O, S, or NH;
c) R$^1$ is CH$_3$,
d) R$^2$ and R$^3$ are independently a hydrogen, halogen, OH, OR', SH, SR', N$_3$, NH$_2$, NHR', CN, OCOR', OCOOR', lower alkyl of C$_1$-C$_6$, halogenated lower alkyl of C$_1$-C$_6$, lower alkenyl of C$_2$-C$_6$, halogenated lower alkenyl of C$_2$-C$_6$, lower alkynyl of C$_2$-C$_6$, halogenated lower alkynyl of C$_2$-C$_6$, lower alkoxy of C$_1$-C$_6$, lower alkyl acid of C$_2$-C$_6$, or lower alkyl acid ester of C$_2$-C$_6$,
e) R$^4$ and R$^5$ are independently a hydrogen, phosphate, diphosphate, or analogs thereof wherein one or two hydrogens on a P(OH) moiety is replaced with an C$_{1-10}$ alkyl, aryl, amino acid ester, steroid, carbohydrate, or lipid group, wherein aryl groups are selected from the group consisting of phenyl, biphenyl, and naphthyl, optionally substituted with one or more moieties selected from the group consisting of hydroxyl, amino, alkylamino, arylamino, alkoxy, aryloxy, nitro, cyano, sulfonic acid, sulfate, phosphonic acid, phosphate, and phosphonate;
f) Base is a heterocycle containing at least one nitrogen; and g) each R' is independently a hydrogen, lower alkyl of C$_1$-C$_6$, or lower cycloalkyl of C$_1$-C$_6$.

16. A compound having a structure consistent with formula (II) or a pharmaceutically acceptable salt thereof,

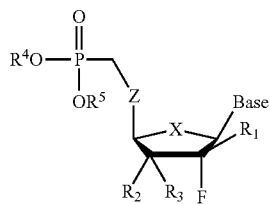

wherein:
a) X is O, S, SO$_2$, or CH$_2$;
b) Z is O, S, or NH;
c) R$^1$ is H or CH$_3$;
d) R$^2$ is selected from the group consisting of hydrogen, halogen, OH, OR', SH, SR', N$_3$, NH$_2$, NHR', CN, OCOR', OCOOR', lower alkyl of C$_1$-C$_6$, halogenated lower alkyl of C$_1$-C$_6$, lower alkenyl of C$_2$-C$_6$, halogenated lower alkenyl of C$_2$-C$_6$, lower alkynyl of C$_2$-C$_6$, halogenated lower alkynyl of C$_2$-C$_6$, lower alkoxy of C$_1$-C$_6$, lower alkyl acid of C$_2$-C$_6$, and lower alkyl acid ester of C$_2$-C$_6$,
e) R$^3$ is selected from the group consisting of halogen, OR, OR', SR, SR', N$_3$, NH$_2$, NHR', CN, OCOR', OCOOR', lower alkyl of C$_1$-C$_6$, halogenated lower alkyl of C$_1$-C$_6$, lower alkenyl of C$_2$-C$_6$, halogenated lower alkenyl of C$_2$-C$_6$, lower alkynyl of C$_2$-C$_6$, halogenated lower alkynyl of C$_2$-C$_6$, lower alkoxy of C$_1$-C$_6$, lower alkyl acid of C$_2$-C$_6$, and lower alkyl acid ester of C$_2$-C$_6$,
f) R$^4$ and R$^5$ are independently a hydrogen, phosphate, diphosphate, or analogs thereof wherein one or two hydrogens on a P(OH) moiety is replaced with an C$_{1-10}$ alkyl, aryl, amino acid ester, steroid, carbohydrate, or lipid group, wherein aryl groups are selected from the group consisting of phenyl, biphenyl, and naphthyl, optionally substituted with one or more moieties selected from the group consisting of hydroxyl, amino, alkylamino, arylamino, alkoxy, aryloxy, nitro, cyano, sulfonic acid, sulfate, phosphonic acid, phosphate, and phosphonate;
g) Base is a heterocycle containing at least one nitrogen; and
h) each R' is independently a hydrogen, lower alkyl of C$_1$-C$_6$, or lower cycloalkyl of C$_1$-C$_6$.

17. A pharmaceutical composition comprising the compound of claim 2, 15, or 16, and at least one of a pharmaceutically acceptable carrier, diluent, vehicle, and excipient.

18. The pharmaceutical composition of claim 17, further comprising a compound selected from the group consisting of cytokines, protease inhibitors, antiviral agents, proteases, caspase inhibitors, antibodies and protease inhibitors.

19. A method of treating a viral infection, or a symptom thereof in a subject in need thereof comprising administering to the subject an effective amount the composition of claim 17.

20. The pharmaceutical composition of claim 17, further comprising at least one of an enzyme therapy agent and an immune system modulator.

* * * * *